United States Patent [19]

Abele et al.

[11] Patent Number: 4,670,892
[45] Date of Patent: Jun. 2, 1987

[54] METHOD AND APPARATUS FOR COMPUTED TOMOGRAPHY OF PORTIONS OF A BODY PLANE

[75] Inventors: Manlio G. Abele, Garden City; Christopher H. Marshall, New York, both of N.Y.

[73] Assignee: Philips Medical Systems, Inc., Shelton, Conn.

[21] Appl. No.: 69,419

[22] Filed: Aug. 24, 1979

Related U.S. Application Data

[60] Division of Ser. No. 850,892, Nov. 15, 1977, Pat. No. 4,433,380, which is a continuation-in-part of Ser. No. 635,165, Nov. 25, 1975, abandoned.

[51] Int. Cl.⁴ ...................... A61B 6/00; G01N 23/08; G03B 41/16
[52] U.S. Cl. ...................................... 378/004; 378/014
[58] Field of Search ................... 250/362, 403, 445 T, 250/363, 369, 360, 252; 378/009, 014, 019, 191, 197

[56] References Cited

U.S. PATENT DOCUMENTS

| | | | |
|---|---|---|---|
| 3,919,552 | 11/1975 | Hounsfield | 250/445 T |
| 3,924,129 | 12/1975 | Le May | 250/445 T |
| 3,952,201 | 4/1976 | Hounsfield | 250/403 |
| 3,956,633 | 5/1976 | Hounsfield | 250/362 |
| 3,973,128 | 8/1976 | Le May | 250/445 T |
| 4,008,400 | 2/1977 | Brunnett et al. | 250/445 T |
| 4,035,651 | 6/1977 | Le May | 250/445 T |

Primary Examiner—Craig E. Church
Assistant Examiner—T. N. Grigsby
Attorney, Agent, or Firm—Jack E. Haken

[57] ABSTRACT

A method and apparatus for computed axial tomography (CAT) image reconstruction applicable to X-ray scanning of the human body. Successive series of calculations determine the values of a characteristic in defined segmented areas of an examination plane. A reduction in the time and equipment requirements for reconstruction calculations may thereby be effected.

Images representative of the difference between the value of the characteristic at a reconstruction point and the average value of the characteristic in adjacent regions ($\Delta\mu$) may be calculated and displayed from measurements taken within a localized contiguous region of the examination plane. Radiation dose to patients and computation time in X-ray computerized axial tomography scanning systems is thus reduced. Differential displays of the type described may be adjusted to image boundaries, in which case they do not suffer from gray scale resolution problems which are typical of prior art displays.

Image artifacts attributable to interpolation errors may be reduced with negligable effect on resolution by incorporating a weighting function, preferentially a Gaussian function, in the image reconstruction.

3 Claims, 24 Drawing Figures

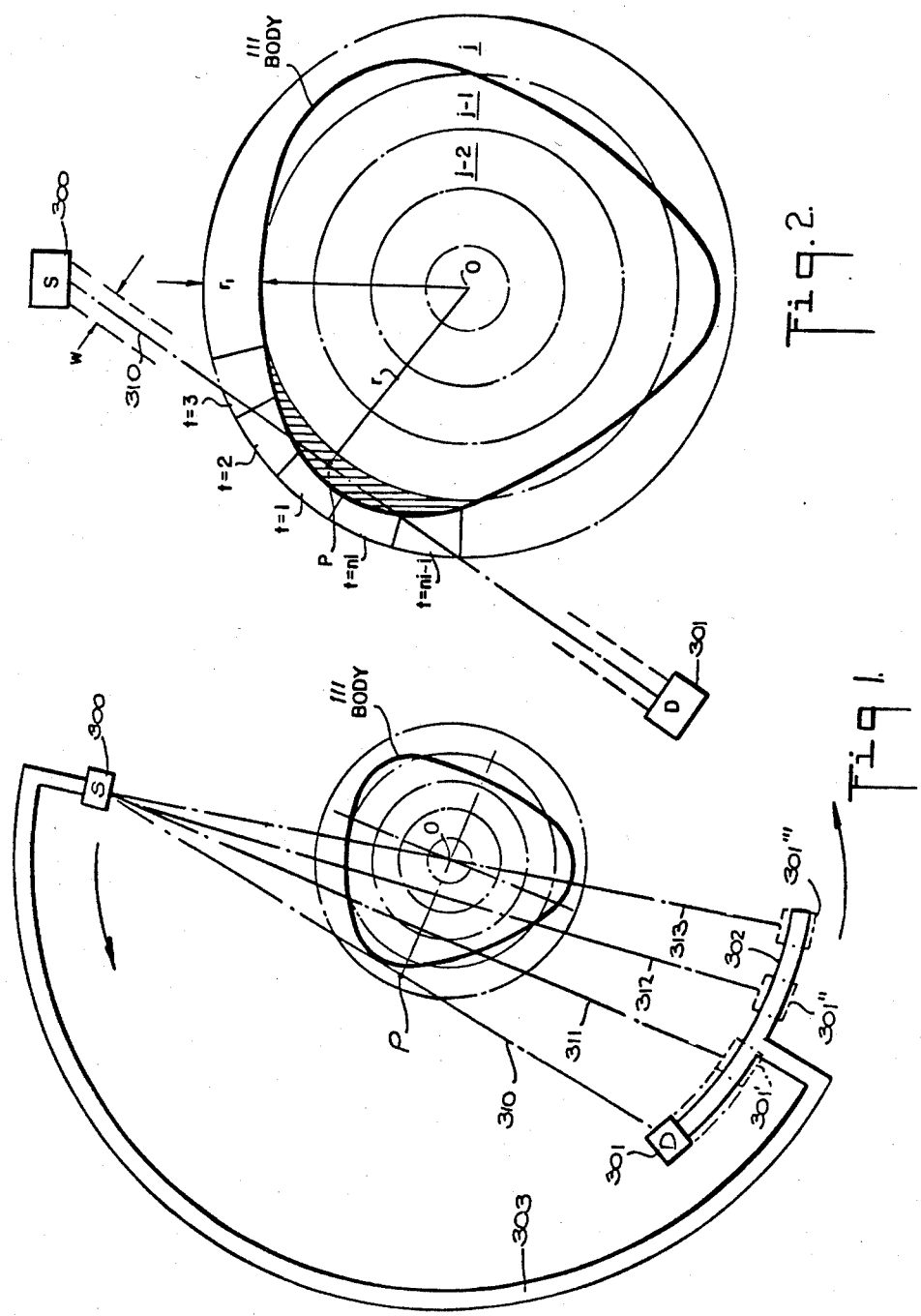

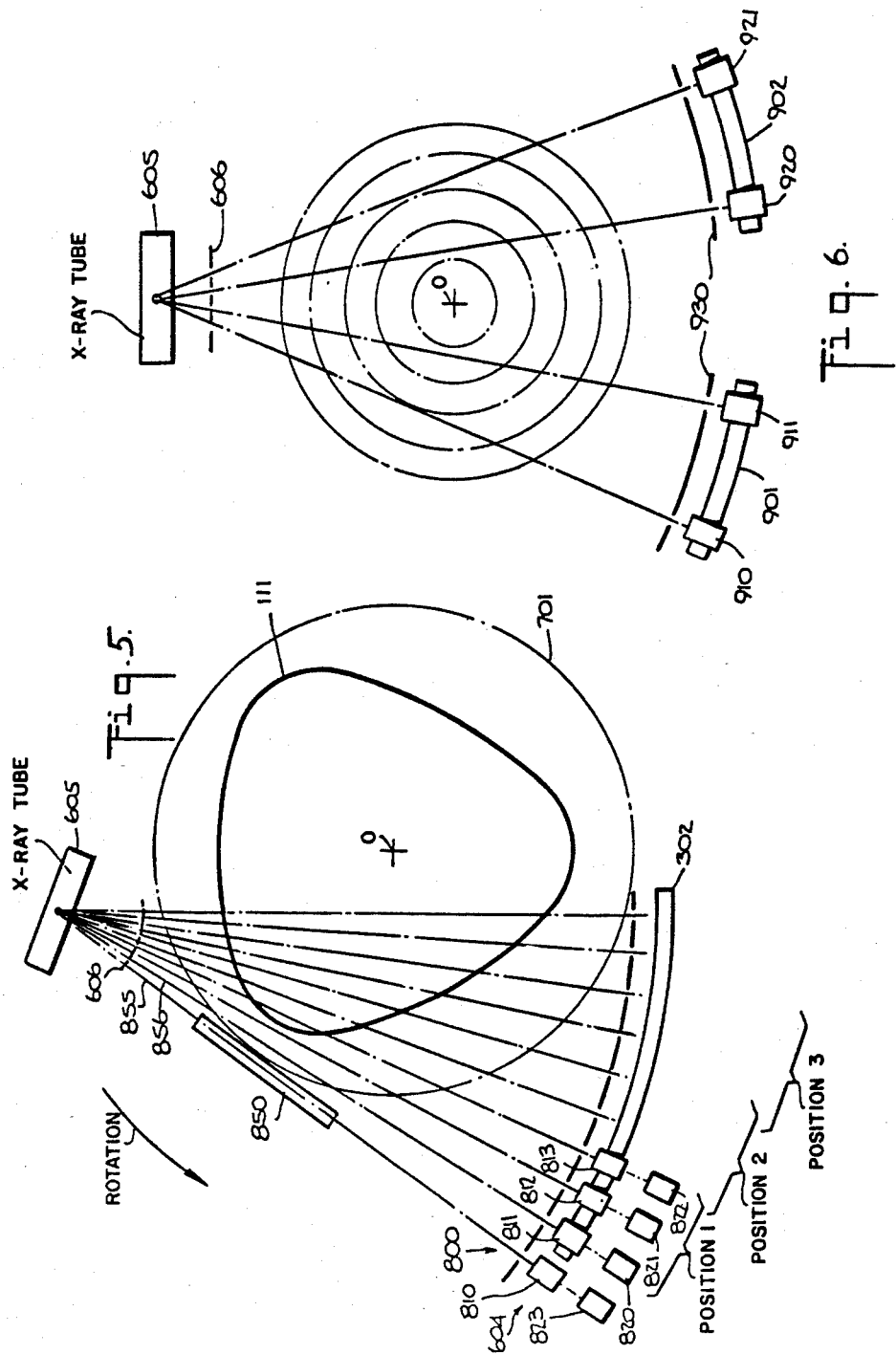

METHOD AND APPARATUS FOR COMPUTED TOMOGRAPHY OF PORTIONS OF A BODY PLANE

RELATED APPLICATIONS

This is a division of application Ser. No. 850,892, filed Nov. 15, 1977, now U.S. Pat. No. 4,433,380 which was a continuation-in-part of U.S. patent application Ser. No. 635,165 filed Nov. 25, 1975 and now abandoned.

BACKGROUND OF THE INVENTION

1. Field of the Invention

The general field of this invention is tomography, that field that relates to obtaining an image of internal body parts in a plane through the body. Specifically, the field of this invention, called transverse axial tomography, relates to a method and apparatus for calculating the value of an incoherent physical characteristic at points within a body from the values of a plurality of line integrals of the characteristic taken through the body. The invention is particularly suited for applying a plurality of X-ray or gamma ray beams through a plane of a body, measuring the attenuation of each beam as it passes through the body, and using the measurement information obtained to construct individual attenuation coefficients for each element of a defined element matrix in the body plane.

2. Description of the Prior Art

A prior art method and apparatus for transverse axial tomography is described in U.S. Pat. No. 3,778,614 issued Dec. 1, 1973. That patent describes a technique to reconstruct a cross-sectional view of a body from a series of transmission measurements obtained by translating a radiation source and detector across the body section and repeating this translation motion at a number of angular orientations in the plane of the section. U.S. Pat. No. 3,778,614 is incorporated herein, by reference, as background material.

The objective of these measurements is to obtain, after computer analysis of thousands of pieces of raw information about beam attenuation through the body plane, the attenuation coefficient associated with each element of a matrix defined in the body plane. The method is useful for internal description of any body, but is primarily useful for identification of internal human body abnormalities. The attenuation coefficients are different for normal body tissue, tumors, fat, etc. and consequently provide identifying information about soft tissues in a human body. Especially useful for identification of brain disease and abnormalities, tomography by computer reconstruction eliminates obvious disadvantages of patient discomfort and morbidity normally associated with brain investigations using pneumography, angiography and radioactive isotope scanning.

In one prior art method, the scan signals are processed to yield visual information and local values of the beam attenuation coefficients over the body section. Detector scan signals are applied to an analog/digital converter to convert the analog scan signals which are proportional to each beam attenuation to digital form and subsequently are recorded in a storage unit. Computer analysis of the entire matrix of scan signals, typically about 28,000 points, yields attenuation coefficients associated with a element matrix defined for the body. These attenuation coefficients are related to the local physical properties in the body plane. After they are computed, the attenuation coefficients are recorded in a storage unit, and subsequently converted to analog signals by means of a digital/analog converter. These signals drive a viewing unit, typically a CRT, with the information content to pictorially display the attenuation coefficient for each matrix element. A permanent record of the display is achieved by means of a camera.

Another prior art method for tomographic image reconstruction makes use of a convolution and backprojection algorithm; as described, for example, in U.S. Pat. No. 3,924,129 which is incorporated herein, by reference, as background material.

High spatial frequency components associated with X-ray scanning measurements can contribute to the production of artifacts in reconstructed images. U.S. Pat. No. 4,002,911 describes a tomographic scanner wherein the intensity profile of an X-ray beam is weighted to limit high frequency components. Weighting of the X-ray beam intensity profile is mathematically equivalent to the inclusion of a weighting function in the convolution integral but is necessarily limited by physical constraints of the X-ray system (i.e. weighting of an X-ray beam is limited to positive weighting functions).

At the present time substantial interest exists in the use of the methods and apparatus of computed tomography for the reconstruction of X-ray images of the human body. The computational methods utilized are, however, equally applicable to other fields wherein the values of an incoherent characteristic function must be calculated from measurments of its line integrals. As used herein, the term "incoherent characteristic" means that the value of the characteristic at each point affects the value of the integral in a manner which is uncorrelated to the value of the characteristic at other points. Although the method and apparatus for the invention are described herein with respect to X-ray scanning apparatus, the use of the invention is by no means limited to that field.

A region of interest, to be examined by the methods of computed tomography, often occupies only a small fraction of the area of a plane extending through the body. For example, a radiologist may only be interested in determining abnormalities within a single body organ. A disadvantage of the prior art method and apparatus is that an entire body plane must be scanned before local values of the attenuation coefficients in a region of interest can be calculated. This is due to the fact that attenuation of the X-ray beams access along the entire beam path and affects the computation of attenuation coefficients at every point in the plane. Thus, if a limited region of interest were totally scanned and the surrounding body areas were only partially scanned (to the extent they were included in the scanning of the region of interest) features in the partially scanned region would produce image artifacts which would significantly distort computed values within the region of interest. Furthermore, severe restriction is placed on the stability of prior art X-ray tube and detector systems and upon the mechanical precision of the scanning devices since consistent data must generally be obtained over the entire scan time in order to accurately compute local attenuation coefficient values. Problems of reconstruction may similarly arise in regions of the body which are subject to motion during a scan.

A scanning motion consisting of translation followed by separate rotation is usually clumsy and subject to mechanical vibration and wear. Because of the mechanical problems involved, it is often difficult to speed the sequence of translation and rotation movement to reduce scanning time. Further problems are reated to the complexity of prior art computer programs necessary for reconstruction and the sophistication of the programs that are required.

SUMMARY OF THE INVENTION

In one embodiment of the invention a thin cross-section or plane through a body is examined by passing X- or gamma ray beams through a body plane. The body plane is depicted for examination purposes as a two-dimensional matrix of elements defined by a plurality of concentric circles which create concentric rings. The outermost ring is denoted as the R ring, the next inner ring to the outermost ring described as the R-1 ring, and so on. Elements in the rings are created by dividing each of the rings. In this manner, the notation $N_R$ represents any number equal to two or greater equally angularly spaced elements of the outermost R ring, the R-1 ring being divided into $N_{R-1}$ elements, and so on.

The method of determining individual attenuation or coefficients for each element in the defined element matrix begins by rotating X- or gamma ray beams around the outside of the body, where a beam is provided for each concentric ring and is so directed in the plane under investigation as to be continuously tangent to its associated ring.

From each beam emerging from the body, at $N_r$ discrete angular intervals during the beams' rotation, a discrete output signal is recorded representing the sum of the attenuation of the elements in each respective concentric ring intersected by the respective beam.

For the outmost R ring, the $N_R$ discrete output signals from the beam tangent to the R ring are used in deriving signals proportional to the individual absorption or transmission elements associated with each of the $N_R$ elements in the R ring.

In response to the $N_{R-1}$ discrete output signals from the beam tangent to the R-1 ring and the signals proportional to the individual attenuation coefficients from the beam tangent to the R-1 ring and the signals proportional to the individual attenuation coefficients associated with the elements in the R ring through which the beam tangent to the R-1 ring passes at each of the $N_{R-1}$ discrete angular intervals, signals are derived proportional to the individual attenuation coefficients associated with each of the $N_{R-1}$ elements in the R-1 ring.

This method is repeated for each succeeding ring in turn for ring R-2 toward the center of the concentric circles. For each concentric ring, signals proportional to the individual attenuation coefficients associated with each of the elements in the ring are derived in response to the $N_r$ discrete output signals from the beam tangent to that ring and the previously derived signals proportional to the individual absorption or transmission coefficients associated with the elements in all other rings through which the beam passes at each of the $N_r$ discrete angular intervals.

The value of the attenuation coefficient at the center of rotation may thus be derived from equations which, in form, resemble the known general convolution-back-projection algorithm, but which include filter (weighting) functions which are derived from the concentric ring model. The computed radial origin of the ring model may, effectively, be shifted to permit calculation of the attenuation coefficient at any point in the plane.

Filter (weighting) functions utilized in the above-described computational method have positive values for measurements passing through the origin of the computational system and negative values for measurements in the adjoining ring. A numerical reconstruction of an image necessarily involves interpolation between these positive and negative values, which interpolation may introduce significant image artifacts. The introduction of an additional weighting function, preferably a Gaussian function, can substantially reduce interpolation errors and errors associated with the propagation of statistical noise through the image without materially affecting image resolution.

The reconstructed value of the attenuation coefficient calculated at any image point is substantially influenced by the actual value of the attenuation coefficient at all other points in the plane. The effect of the attenuation coefficient at a remote point upon the calculated value of an attenuation coefficient at a reconstruction point is substantially a function of the reciprocal of the distance between the points. Generally, clinical requirements dictate that all points in a body plane be utilized for the reconstruction of attenuation coefficients at any other point in the plane.

However if, instead of reconstructing the actual values of the attentuation coefficient at any point, the reconstruction instead calculates a differential image ($\Delta\mu$) from values which represent the difference between the value of the local attenuation coefficient at a reconstruction point and the average value of the attenuation coefficient in a surrounding area (a process which roughly corresponds to the calculation of the second spatial derivative of the local attenuation coefficient) the effect of the attenuation coefficient at remote points in the plane becomes dependent upon the reciprocal square of the distance separating the remote points from the reconstruction point. The area scanned to produce $\Delta\mu$ images of a region of interest within the body may thus be confined to the region of interest and a small surrounding transition area, the dimensions of the transition area being determined by the required precision of the reconstruction at the edge of the region of interest. Since X-ray radiation for such measurements may, thereby, be confined to a small region of the body; the total radiation dose received by the patient and the associated scan time may be significantly reduced.

The methods of computed tomography generally yield images having a far wider range of values than it is possible to display on a conventional image output device. A radiologist examining computed tomography images must, therefore, often shift the range and threshold of a gray-scale display to allow imaging of significant clinical features. A detailed discussion of the nature of the gray-scale resolution problem and a prior art device for overcoming that problem is described in U.S. Pat. No. 4,030,119 which is incorporated herein, by reference, as background material.

$\Delta\mu$ displays, which display the difference between the local value of an attenuation coefficient and the average value of attentuation coefficients in surrounding areas as signed, gray-scale levels (for example with neutral gray representing zero; black representing negative values; and white representing positive values) tend to accentuate boundary regions, and thus do not suffer from the gray scale compression problems of prior art displays of the attenuation coefficient. Area boundaries may thus be readily visualized in a $\Delta\mu$ gray-scale display which might otherwise be invisible in a conventional gray-scale display of attenuation coefficients.

The $\Delta\mu$ image affords the following properties:

The $\Delta\mu$ image provides the local departure of tissue properties from an average value of the surrounding tissues;

The $\Delta\mu$ image can provide the outline of tissue anomalies;

The scanning can be confined to a limited region of the body region with no significant distortion of the $\Delta\mu$ image reconstruction within the same region;

In a $\Delta\mu$ image which provides the outline of body organs and anomalies the effect of statistical noise is less important than in a conventional image. The $\Delta\mu$ image is used only to locate the boundaries rather than to determine the local value of $\Delta\mu$;

The rapid convergence of the filter functions which determine the backprojection for the reconstruction of $\Delta\mu$ reduces the number of significant terms of the series and the time required for the reconstruction calculations.

A novel apparatus is disclosed for performing the method. A rotating frame is provided supported with respect to a fixed frame by means of a bearing and is rotated therein. A source of X- or gamma rays is mounted on a first arm attached to the rotating frame. The source generates one or more beams in a plane perpendicular to the axis of rotation. The beams are intercepted by a system of detectors mounted on a second arm attached to the rotary frame. The beams are defined by collimators associated with both the ray sources and the detection system and directed so as to be effectively tangent to concentric rings defined about the axis of rotation of the rotating frame in a plane of a body placed in or near the axis of rotation between the source and detector system.

In an embodiment of the detector system a reference crystal detector and a plurality of measurement crystal detectors are provided in groups, which may be moved in position on a track so as to intercept different beams passing through the body on different rotations of the rotating frame. Photomultiplier tubes are provided, one for each measurement crystal detector, to generate electrical signals proportional to the corresponding beam intensity. Means are provided to magnetically store the beam attenuation signals in digital form. A stored program digital computer is provided for deriving signals proportional to attenuation or transmission coefficients for the defined element matrix in the body plane. These signals are stored, and are then useful to provide a representation of the absorption characteristics of the body plane.

BRIEF DESCRIPTION OF THE DRAWINGS

This invention, as well as its objects and features, will be better understood by reference to the following detailed descriptions of the preferred embodiments of this invention taken in conjunction with the accompanying drawings in which:

FIG. 1 is an X- or gamma ray source/detector orientation, constructed in accordance with this invention, for rotation of a beam pattern about a body in which an element matrix is defined by concentric circles and equally spaced radii;

FIG. 2 shows in more detail the defined element matrix, constructed in accordance with this invention, for measurement of absorption coefficients in a body plane;

FIG. 5 is a schematic diagram of beam generation and detection in accordance with this invention;

FIG. 6 is a schematic diagram of an alternative embodiment of beam generation and detection in accordance with this invention;

LIST OF PRINCIPAL SYMBOLS

Figure 3:
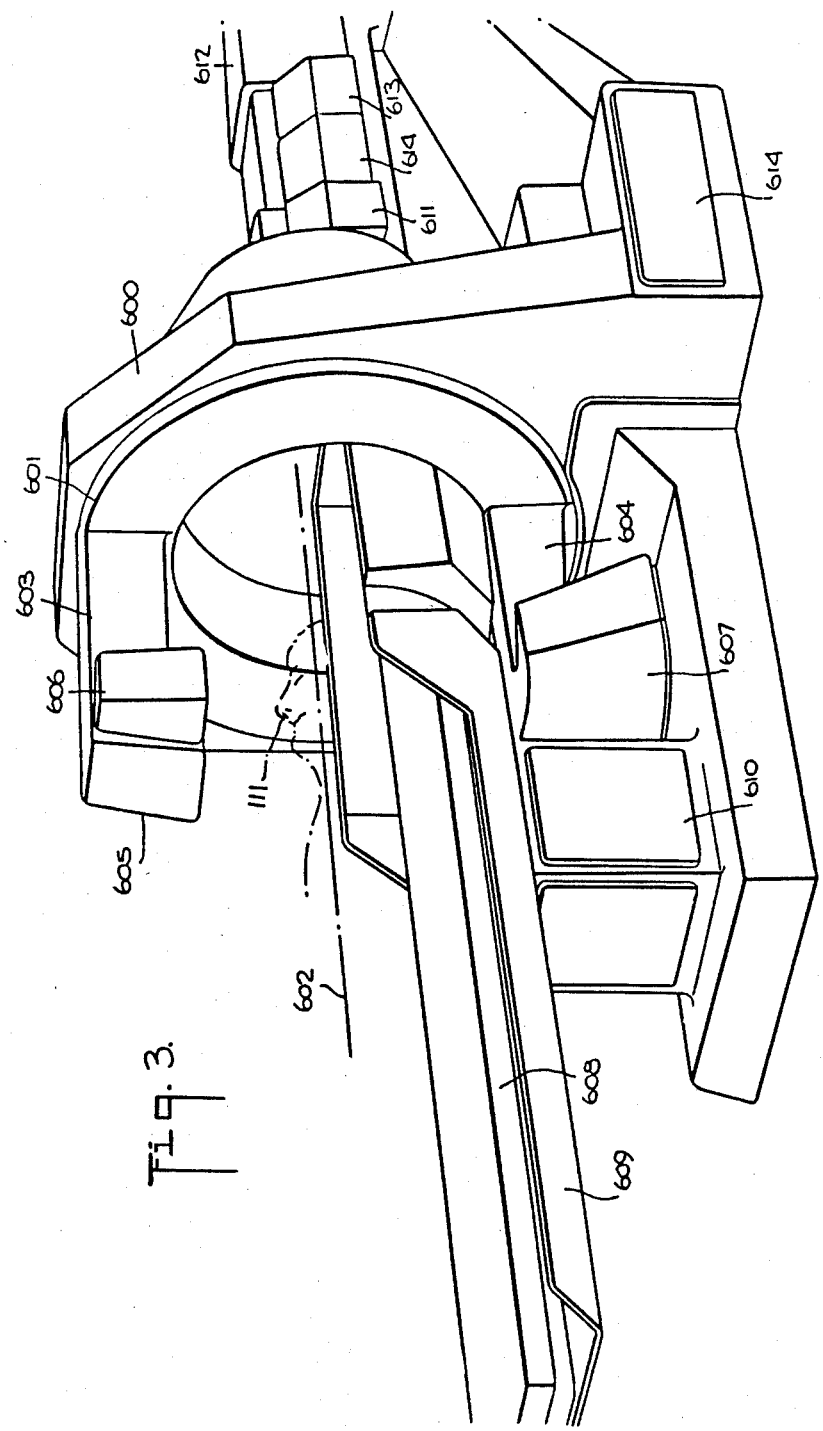
FIG. 3 is a perspective of physical apparatus, constructed in accordance with this invention, for rotating a beam pattern through a plane of a body and the measurement of beam attenuations after the beams pass through it.

In the following discussion the principal symbols are summarized and defined as follows:

f: weighted attenuation value for $\mu$ reconstruction defined by Equation (2.22).

$F_j$: weighting coefficients to construct f; defined by Equation (2.23).

$\tilde{F}_j$: weighting coefficients to construct f; defined by Equation (3.2).

g: weighted attenuation value for $(\mu - <\mu>)$ reconstruction; defined by Equation (2.28).

$G_j$: weighting coefficients to reconstruct g; defined by Equation (2.29).

$\tilde{G}_j$: weighting coefficients to reconstruct g; defined in Equation (3.6).

$H_j$: weighting coefficients for non-uniform radial sampling intervals; defined by Equation (6.21).

I: X-ray beam intensity l: index of radius of averaging circle for $<\mu>$.

N: number of angular sampling increments r: radial coordinate of polar (r, $\theta$) system in the image plane.

$r_1$: radial increment x: coordinate of Cartesian (x,y) system.

y: coordinate of Cartesian (x,y) system.

$\alpha_i$: geometrical factor relating interception of beam in rings.

$\beta$: X-ray beam attenuation.

$<\beta>$: intensity-averaged measured value of $\beta$ $\Gamma_j$: weighting coefficients; defined by Equation (6.11).

$\delta, \Delta$: incremental difference operators.

$\theta$: angular coordinate of polar (r, $\theta$) system in the image plane.

$\theta_i$: angular increment.

$\theta_{i,j}$: parametric coefficients; defined by Equation (2.6).

$\lambda$: generalized averaging dimension; defined by Equation (6:13).

$\mu$: local value of linear attenuation coefficients.

$<\mu>$: average value of $\mu$ over a circle of radius $l_{r1}$ about each reconstruction point.

$\xi$: distance along a ray path from source to detector $\rho$: radial coordinate of polar ($\rho$, $\psi$) system in the the scanning plane.

$\psi$: angular coordinate of polar ($\rho$, $\psi$) system in the scanning plane.

$\psi_1$: angular increment.

$\psi_0$: angular sector scanned in an incomplete scanning.

$\omega$: weighting function; defined by Equation (6.1).

DESCRIPTION OF THE PREFERRED EMBODIMENTS

Concentric Ring Scanning

FIG. 1 shows a sketch of a body plane 111 to be examined by transverse axial tomography according to this invention. The body 111 is assumed to be placed between a source 300 of X- or gamma rays and a detector 301, which may be a scintillator and a photomultiplier and which preferably also includes a collimator. For illustrative purposes, detector 301 is assumed to be movable on a track 302 such that beams may be detected which pass at various angles from the source through body 111. Multiple detectors, each with an associated collimator can of course be provided as detectors 301, 301', 301'', etc., or multiple detectors may be movable on track 302. The X-ray source 300 and detectors 301, are attached to a rotating ring 303 which is rotatable about an axis O perpendicular to the body plane 111. Body 111 is shown in FIG. 1 coexistent with axis O, but it may be placed anywhere within the beam range of source 300 and detector 301.

As shown in FIG. 1 a series of concentric circles is defined about axis of rotation O. As ring 303 rotates about the axis of rotation O, the X-ray beam or beams is continuously directed (as shown at one orientation angle of rotation) perpendicular to subsequent radii from axis O at point P at all times as ring 303 rotates about axis O. As a result, a beam such as 310 is at all times tangent to the outer ring about center O as the source-detector system rotates.

FIG. 2 shows in more detail the concentric system defined about axis of rotation O. Beam 310 is shown at a particular orientation during its rotation about body 111 and is perpendicular to a particular radius vector r at point P. By appropriate collimation, the beam width w can be made to approximate the concentric ring width $r_1$. The example depicted in FIG. 2 shows beam 310 passing through the outermost concentric ring (i). Perpendicular to radius vector r, beam 310 is depicted as passing through elements labelled $t=n_i-1$, $n_i$, 1, 2 and 3. These elements are among those elements in the i ring, totalling $n_i$ elements.

In order to describe the interior of body 111 according to the matrix of elements throughout the concentric ring-radius vector system shown in FIG. 2, each small element is assigned an unknown value of attenuation coefficient. For example, the attenuation coefficient for element t=1 in the i th ring is designated $\mu_{i,1}$; for element t=2, $\mu_{i,2}$; for the t th element, $\mu_{i,t}$. The measured beam attenuation for beam 310 shown will be given by the sum of the average value of the linear attenuation constants $\mu$ for each element through which the beam passes.

During rotation about axis O, the beam attenuation between source 300 and detector 301 is obtained at $n_i$ different positions, only one of which is shown in FIG. 2. Beam attenuation for each measurement, designated $\beta_{i,z}$ is simply the sum of the linear attenuation constants for each element through which the beam passes, multiplied by an individual geometrical factor determined by the interception of the beams with each cell. The rotation-measurements steps of the beam 310, as source 300 and detector 301 rotate about O, are identified by an index z. This index z runs from 1 in steps of 1 until $z=n_i$, equal to the number of elements in ring i. Thus, the measurement of the beam attenuation at each position of the first intercepting ring leads to the equations, $$\sum_{t=1}^{n_i} (\alpha_{i,t-z})(\mu_{i,t}) = \beta_{i,z} \quad (1.1)$$

where $Z = 1, 2, \ldots n_i$

The term $\alpha_{i, t-z}$ represents the geometrical factor determined by the interception of the beam 310 with each element t as it rotates in z steps about ring i.

Since t is taken equal to z, that is, the number of elements in ring i is t, and the number of measurements around ring i is equal to z, equation (1.1) represents a system of equations $z=n_i$ in number, having $t=n_i$ unknown parameters $\mu_{i,t}$. The solution of the system of equations (1.1) yields the values of $\mu$ associated with each element on the i=1 ring.

In the next scanning ring, the i−1 ring, the measurement of the beam attenuation leads to the new system of equations, $$\sum_{t=1}^{n_{i-1}} (\alpha_{i-1,t-z})(\mu_{i-1,t}) = \beta_{i-1,z} - \sum_{t=1}^{n_i} (\alpha'_{1,t-z})(\mu_{i,t}) \quad (1.2)$$

for, $z=1,2, \ldots n_{i-1}$ wherein $\alpha'_{1, t-z}$ is the geometrical factor determined by the interception of the beam (e.g. beam 311, FIG. 1) in the new ring, i−1, with the elements of the outer ring i.

The values $\mu_{i,t}$ have been determined by the solution of Equations (1.1); the solution of the system of Equations (1.2) provides the values of $\mu_{i-1, t}$ in the ring i−1. The measurement in each scanning ring with decreasing radii provides a system of equations similar to (1.2) with terms on the right hand side containing known values of $\mu$ in the elements pertaining to the outer rings. It is apparent that the number of elements of each outer ring which contributes to the attenuation along an inner ring decreases rapidly as the scanning radius approaches zero, i.e. as the scanning beam approaches the center of rotation.

Thus, the local properties are fully determined upon completion of each scanning ring without having to wait for the total scanning of the body section.

The number of equations in each set, similar to equation (1.2), is relatively small and can be arranged to decrease as the interior rings with smaller radii are measured. Assuming for example a scanning radius of the outer ring of the order of 150 mm and an element width on the order of 3 mm, each independent equation set for the outer rings consists of only several hundred equations. The solution for the unknown $\mu$'s for each ring sequentially from the outside ring toward the inside rings, requires far less computational time than prior art X-ray tomographic systems. As the inner rings are measured, it is possible to decrease the number of measurements taken around the ring (i.e. define $n_i$ to be less for the inner rings than for the outer rings, thereby keeping the element size approximately constant) with the result that the equation set size is reduced. Computational time is correspondingly reduced for solution of inner ring $\mu$'s.

Concentric Ring Scanner

Illustrated in FIG. 3 is a perspective drawing of a concentric ring scanning apparatus. A fixed frame 600 supports a rotating frame 601 which is free to revolve about an axis of rotation 602. A motor drive 614 is provided in fixed frame 600 to propel rotating frame 601. Attached to rotating frame 601 are two arms 603, 604 spaced approximately 180 degrees from one another. Arm 603 supports an X-ray tube 605 and an associated X-ray tube collimator control 606. Arm 604 carries a detector assembly 607 and associated detector collimators.

A couch 608 is provided to allow a human body 111 to be positioned between X-ray tube 605/-x-ray tube collimator control 606 and detector assembly 607. Couch 608 is supported by couch support 609. A couch control system 610 is provided which translates the couch 608 parallel to the axis of rotation 602, thereby positioning body 111 to a point where beams from X-ray tube 605 may intersect a desired plane through the body 111. In addition, the couch control system 610 translates the couch 608 in any direction in a plane perpendicular to the axis of rotation, thereby positioning the axis of rotation close to the desired area of the body 111.

Since the X-ray tube 606 is rotatable about center line 602 means are provided to cool it and provide it with high voltage electrical power while it is rotating. These means, shown in modular form, are a cooling water rotating assembly 611 and a high voltage slip ring assembly 612. Means must also be provided to send command and control signals to X-ray tube 605 and its associated collimator assembly and collimators associated with detectors 607 while they are rotating. Command and control slip ring assembly 614 is provided for that purpose. Likewise data transmission slip ring assembly 613 is provided to provide a means for transmission of data signals from detectors 607 while they are rotating.

Figure 4:
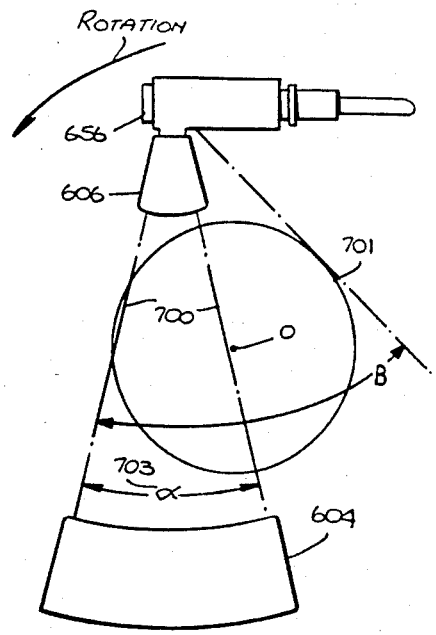
FIG. 4 is an X-ray tube beam spread, constructed in accordance with this invention, as it rotates about the body under investigation.

FIG. 4 shows a preferred orientation of X-ray tube 656 and its associated collimator control 606 with respect to detector and detector collimator apparatus 604.

The X-ray beam 700 produced by the source is fan shaped and subtends an apical angle $\alpha$. The tangents to the circle of the aperture opening 701 which pass through the source define an apical angle $\beta$. The relationship between the apical angle $\alpha$ and the apical angle $\beta$ is that the apical $\beta$ angle $\alpha$ is less than the apical angle $\beta$.

As indicated in FIG. 3, X-ray tube 656 and detector assembly 604 are rigidly connected to each other by arms 603, and 604 on rotating frame 601. Rotation of the frame 601 about center line 602 (point 0 to FIG. 4) causes the X-ray beam 700 to sweep out a fan-shaped pattern, which substantially covers any body placed within an aperture 701. The scanning proceeds with sequential rotations of the X-ray beams, with at least one beam being directed to at least one particular ring. On each subsequent rotation around the outside of the body the beam is redirected to at least one particular additional ring. In a preferred embodiment, the fan shaped beam subtends an approximately 30 degree arc as the X-ray tube-detector assemblies are rotated at speeds of up to one complete rotation per second for approximately 10 revolutions. The aperture opening 701 is approximately 26 inches in diameter. The arms 603, 604 attaching the X-ray housing 605 and detector system 607 are approximately thirty inches long. The rotating frame 601 is supported with respect to fixed frame 600 by a single, thirty-five inch diameter, precision ball bearing.

FIG. 5 illustrates the multiple beam scanning aspects of this invention. The X-ray tube 605 emits a continuous fan-shaped array of X-rays, but this continuous array must be divided into beams in order for the methods described previously in this specification to be applicable. Collimators 606 and 800 are provided to create a plurality of beams passing through a cross section of a body 111 placed within aperture 701. For illustrative purposes three detector system pairs consisting of crystal scintillators and photomultipliers (811, 820; 812, 821; 813, 822) are shown in position 1. A reference scintillator 810 and its associated photomultiplier 823 are stationary. The detector pairs remain in position 1 for the first rotation of rotating frame 601 (FIG. 3). At the start of the second rotation, the detector system pairs are shifted along track 302 to position 2 for detection of beams at that position. The detectors are shifted to position 3 at the start of the third revolution, and so on. This shifting of detectors at the end of one rotation and the beginning of another rotation assures that the entire body placed within aperture 701 may be scanned.

Figure 4A:
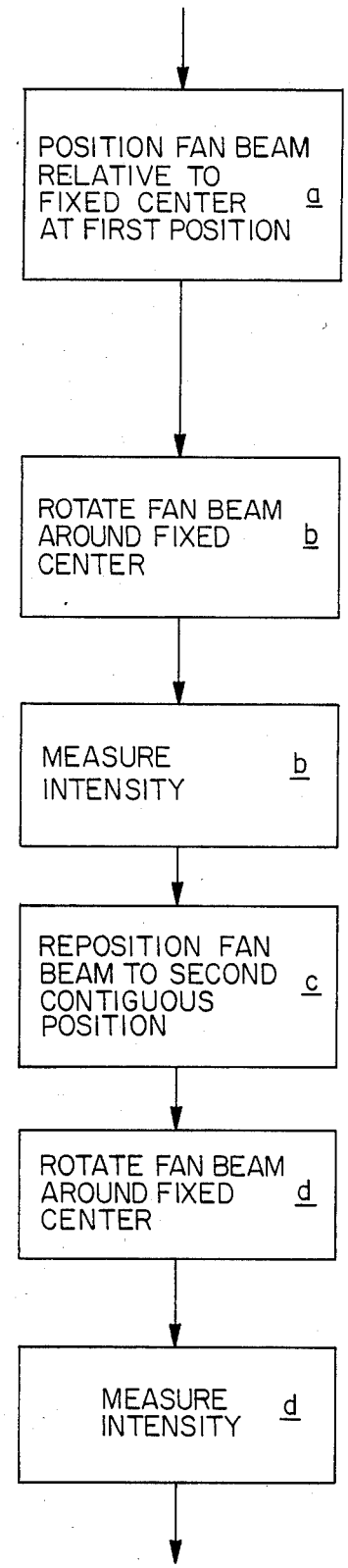

FIG. 4a illustrates a method for scanning a body using a source of penetrating radiation that produces a plurality of coplanar beams defining a fan beam by:

(a) positioning the fan beam relation to a spacially fixed center at a first position;

(b) rotation the fan beam about the fixed center and measuring the intensity of each beam after it passes through the cross section;

(c) repositioning the fan beam relative to the fixed center to a second position; and (d) repeating step (b).

The rotations described in step (b) may be through substantially 360° so that each rotation causes the fan beam to sweep out an area of the cross section defined by reference circles concentric with the fixed center and tangent to the extremities of the fan mean. The positions of the fan beam may be selected such that the swept out areas are continuous.

In practice the translatory motion of the X-ray source and/or detectors need not be accomplished in stepwise fashion after each rotation. Rather, the translatory and rotational motions may be accomplished simultaneously so that the point of tangency of each X-ray beam moves in a smooth spiral. The data thus obtained may then be interpolated, for example by a linear interpolation in a digital computer, to calculate equivalent data at points in the concentric ring coordinate system.

A preferred embodiment of the scanning system of FIG. 5 consists of an arrangement capable of scanning a test object contained within a 20 inch diameter circle about axis of rotation O. Thirteen detector units are provided one of which is the reference pair 810, 823, the other twelve of which are moveable to ten positions along detector track 302. Each detector system is used to scan a 2.5 degree sector of the total scanning area, ten revolutions of the X-ray tube/detector system 604 being used to scan the entire body.

Detector 810 and photomultiplier 823 are used to generate a reference beam attenuation signal for all the other detectors to account for any variations with time in beam strength eminating from X-ray tube 605. As shown in FIG. 5 a particular beam 855 is collimated by tube collimator 606 and passes through an attenuator 850 located outside the location of the body being examined. The absorption characteristics of attenuator 850 are preferably selected to be similar to that of the body being examined. Tissue equivalent plastic is an example of an attenuator material suitable for this purpose. Detector pair 810,823 generates a signal, the intensity of which is proportional to the strength of the X-ray beam after absorption by attenuator 850.

Each detector pair for the beams passing through the body under investigation generates a signal proportional to a particular beam's intensity after it passes through the body. The crystal scintillators produce a high-frequency signal (visible light spectrum) proportional to the number of photons in the X- or gamma ray beams impinging on them. The photomultipler tubes associated with each crystal scintillator, react to the light energy from their respective scintillators to generate an electrical signal proportional to beam strength impinging on the scintillators. For example, an electrical signal proportional to the beam strength of beam 856 is generated at the output of photomultiplier tube 820. Similarly, crystal scintillator/photomultiplier pairs generate output signals proportional to the strength of other beams at position 1, position 2, etc. for the entire beam pattern after successive rotations of system 604.

In a preferred embodiment of this invention, the X-rays generated by X-ray tube 605 are collimated by means of a 15 cm long collimator 606 at the X-ray tube source, and a 20 cm long collimator 800 at the detector system 604. This collimation at the X-ray source and detector defines radiation beams having a rectangular profile of 1 mm by 5 mm width as measured by scanning a lead edge at the mid-point of the beam path.

The range of values for which the photomultiplier must respond can be reduced by covering the body being examined with a material, the absorption of which is known, so that beam intensities received by the detectors are kept as constant as possible as they pass through the body.

FIG. 6 shows an alternate embodiment of detector orientation. Detectors 910 and 911 are located on track 901, and detectors 920 and 921 are located on track 902. As shown, detectors 910 and 911 measure beam attenuation through circular rings, defined about rotation axis O, different from those measured by detectors 920 and 921. Multiple positions on each track can be established and the detectors shifted in position with each rotation until a defined ring matrix is entirely scanned and detected. Collimators 606 are provided at the X-ray source and collimators 930 at the detectors are also provided.

An X-ray tube appropriate for the particular embodiment discussed above is a modified version of a Philips 160 kV Beryllium Window Tube, Model MCN 160.

Appropriate detectors include scintillation detectors such as NaI, Ca $F_2$, BGO and proportional counters such as high pressure xenon detectors and solid state detectors.

Figure 7:
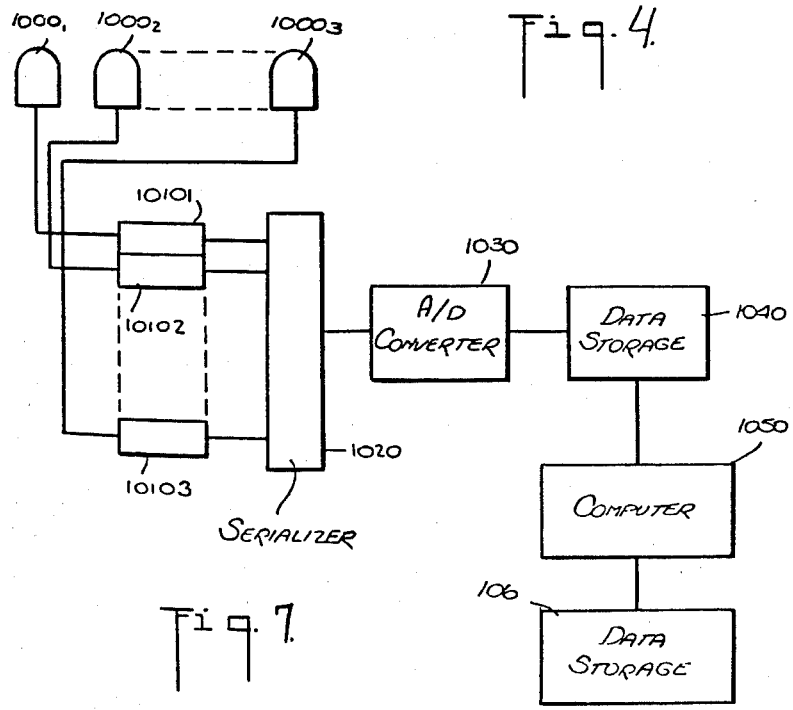
FIG. 7 is a schematic diagram of measurement data collection, recording and processing in accordance with this invention.

FIG. 7 indicates how the beam attenuation data measured by the detector systems, including the photomultipliers $1000_1$ $1000_2$, ... $1000_3$, are processed during the rotational scanning of a body. An information signal is generated in each photomultiplier at each defined increment for each rotation of the X-ray source/detector system. These signals are individually amplified by amplifiers $1010_1$, $1010_2$, ... $1010_3$, are each taken up in turn by serializer 1020, converted to digital form by analog to digital converter 1030, and stored in a data storage medium 1040 such as magnetic tape, disk, or drum or solid state memory. This data collection process continues for each detector position, for each defined increment step, for the complete rotation. During or after the data collection process, a computer 1050 under direction of a stored reconstruction code program, processes the collected data according to the methods discussed elsewhere in this specification. The output of the computer 1050 is a sequence of digital signals proportional to the attenuation coefficients of each element in the defined circular ring matrix. These signals are stored in a data storage unit 106 which may be identical to unit 1040 or similar to it. The output digital signals can then be printed and/or converted to analog form and used to drive a display on a cathode-ray tube, thereby pictorially indicating the attenuation coefficients for the defined matrix in the cross section of the body being investigated.

GENERAL RECONSTRUCTION METHOD

The concentric ring reconstruction may be generalized for image reconstruction at any point. In the plane x, y of FIG. 8, the cross-section of a body is confined within the boundary S. Line $\beta$ represents the axis of an X-ray beam, which ideally is assumed to be of negligible cross section. The total attenuation of the beam passing through the body is given by $$\beta = \ln \frac{I_o}{I_e} \quad (2.1)$$

where $I_o$ and $I_e$ are the beam intensity at the entrance and exit of the body section respectively. The total attenuation $\beta$ can be written in terms of the local value of the attenuation coefficient $\mu$ as the line integral $$\beta = \int_{P_1}^{P_2} \mu d\xi \quad (2.2)$$

Assume now that at each point P of the body section the values of $\beta$ are available for any line $\xi$ passing through P in any angular direction. From these values of $\beta$ it is possible to compute the value of $\mu$ at each point of the body section. $O_r$ is an arbitrary point where $\mu$ is to be computed. Define a family of circles with center $O_r$ and radii $$r_j = jr_1 \; (j = 1, 1, 2, \ldots) \quad (2.3)$$

where $r_1$ is an arbitrary dimension which is small compared to the body section dimensions. Thus, the body section is divided into a large number of circular sectors.

Figure 8:
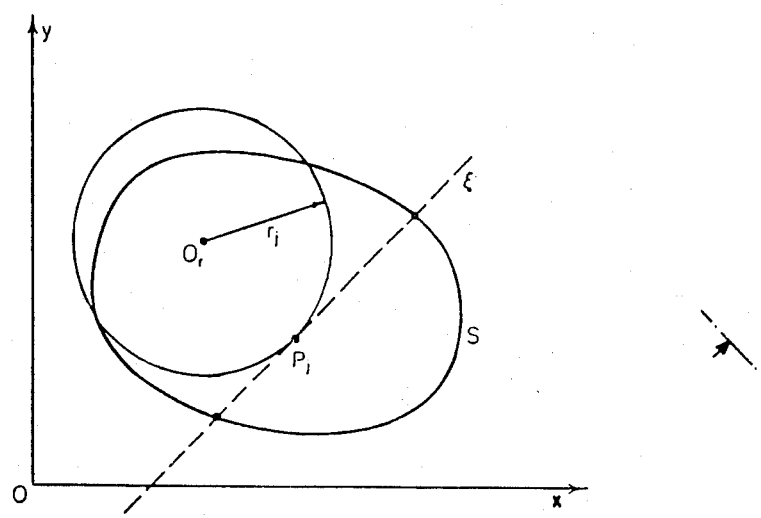
FIG. 8 schematically describes a general scanning procedure.

At a point $P_j$ over the circle of radius $r_j$ let $\beta_j$ be the measured attenuation along a line tangent to the circle as indicated in FIG. 8.

Define $\mu_h$ as the average value of $\mu$ in the region between the circle of radius $hr_1$ and the circle of radius $(h+1) r_1$. Thus, $\mu_o$ is the average value of $\mu$ within the first circle of radius $r_1$. By averaging over $2\pi$ the values of $\beta_o$ measured with the X-ray beams passing through $O_r$ one has $$\int_0^{2\pi} \beta_o d\psi = 4\pi r_i \sum_0^\infty \mu_h \quad (2.4)$$

Similarly the average over $2\pi$ of the values of $\beta_j$ is related to the average values of $\mu_h$ (for h $\geq$ j) by the equation $$\int_0^{2\pi} \beta_j d\psi = 4\pi r_1 j \sum_{h=j}^\infty \theta_{j,h-j+1} \mu_h \quad (2.5)$$

where $$\theta_{j,k} = \frac{1}{j} [\sqrt{(j+k)^2 - j^2} - \sqrt{(j+k-1)^2 - j^2}] \quad (2.6)$$

from Equation (2.4), with the aid of Equation (2.5), one obtains $$\mu_o = \frac{1}{4\pi r_1} \int_0^{2\pi} \left( \beta_o - \sum_1^\infty \frac{K}{j} \beta_j \right) d\psi \quad (2.7)$$

where $$K_j = \frac{1}{\theta_{j,1}} (1 - \theta_{1,j} K_1 - \theta_{2,j-1} K_2 - \ldots - \theta_{j-1,2} K_{j-1}) \quad (2.8)$$

with $$K_1 = \frac{1}{\theta_{1,1}} = \frac{1}{\sqrt{3}} \quad (2.9)$$

The asymptotic value of coefficients $K_j$ is $$K_j = \frac{2}{\pi} \frac{1}{j} (j >> 1) \quad (2.10)$$

The numerical values of $K_j$ up to $j=100$, are presented in Table I.

TABLE I

| j | $K_j$ | $\frac{j K_j}{1 j}$ | j | $K_j$ | $\frac{j K_j n}{1 j}$ |
|---|---|---|---|---|---|
| 1 | .57735E+00 | .57735E+00 | 51 | .12502E−01 | .98763E+00 |
| 2 | .32826E+00 | .74148E+00 | 52 | .12261E−01 | .98787E+00 |
| 3 | .22153E+00 | .81532E+00 | 53 | .12029E−01 | .98809E+00 |
| 4 | .16542E+00 | .85668E+00 | 54 | .11806E−01 | .98831E+00 |
| 5 | .13153E+00 | .88298E+00 | 55 | .11591E−01 | .98852E+00 |
| 6 | .10903E+00 | .90116E+00 | 56 | .11384E−01 | .98873E+00 |
| 7 | .93064E−01 | .91445E+00 | 57 | .11183E−01 | .98892E+00 |

TABLE I-continued

| j | $K_j$ | $\frac{j K_j}{1 j}$ | j | $K_j$ | $\frac{j K_j n}{1 j}$ |
|---|---|---|---|---|---|
| 8 | .81161E−01 | .92460E+00 | 58 | .10990E−01 | .98911E+00 |
| 9 | .71953E−01 | .93259E+00 | 59 | .10804E−01 | .98930E+00 |
| 10 | .64621E−01 | .93905E+00 | 60 | .10623E−01 | .98947E+00 |
| 11 | .58645E−01 | .94438E+00 | 61 | .10449E−01 | .98964E+00 |
| 12 | .53681E−01 | .94886E+00 | 62 | .10280E−01 | .98981E+00 |
| 13 | .49493E−01 | .95267E+00 | 63 | .10117E−01 | .98997E+00 |
| 14 | .45912E−01 | .95594E+00 | 64 | .99583E−02 | .99013E+00 |
| 15 | .42814E−01 | .95880E+00 | 65 | .98048E−02 | .99028E+00 |
| 16 | .40109E−01 | .96131E+00 | 66 | .96560E−02 | .99042E+00 |
| 17 | .37725E−01 | .96352E+00 | 67 | .95117E−02 | .99056E+00 |
| 18 | .35610E−01 | .96550E+00 | 68 | .93716E−02 | .99070E+00 |
| 19 | .33719E−01 | .96728E+00 | 69 | .92356E−02 | .99084E+00 |
| 20 | .32019E−01 | .96888E+00 | 70 | .91035E−02 | .99097E+00 |
| 21 | .30482E−01 | .97033E+00 | 71 | .89751E−02 | .99109E+00 |
| 22 | .29087E−01 | .97165E+00 | 72 | .88502E−02 | .99122E+00 |
| 23 | .27813E−01 | .97286E+00 | 73 | .87288E−02 | .99134E+00 |
| 24 | .26647E−01 | .97397E+00 | 74 | .86107E−02 | .99145E+00 |
| 25 | .25575E−01 | .97499E+00 | 75 | .84958E−02 | .99157E+00 |
| 26 | .24585E−01 | .97594E+00 | 76 | .83838E−02 | .99168E+00 |
| 27 | .23670E−01 | .97682E+00 | 77 | .82748E−02 | .99178E+00 |
| 28 | .22820E−01 | .97763E+00 | 78 | .81686E−02 | .99189E+00 |
| 29 | .22029E−01 | .97839E+00 | 79 | .80651E−02 | .99199E+00 |
| 30 | .21291E−01 | .97919E+00 | 80 | .79641E−02 | .99209E+00 |
| 31 | .20601E−01 | .97977E+00 | 81 | .78657E−02 | .99219E+00 |
| 32 | .19955E−01 | .98039E+00 | 82 | .77697E−02 | .99228E+00 |
| 33 | .19348E−01 | .98098E+00 | 83 | .76760E−02 | .99237E+00 |
| 34 | .18776E−01 | .98153E+00 | 84 | .75845E−02 | .99246E+00 |
| 35 | .18238E−01 | .98205E+00 | 85 | .74952E−02 | .99255E+00 |
| 36 | .17729E−01 | .98254E+00 | 86 | .74079E−02 | .99264E+00 |
| 37 | .17248E−01 | .98301E+00 | 87 | .73227E−02 | .99272E+00 |
| 38 | .16793E−01 | .98345E+00 | 88 | .72394E−02 | .99280E+00 |
| 39 | .16361E−01 | .98387E+00 | 89 | .71579E−02 | .99289E+00 |
| 40 | .15951E−01 | .98427E+00 | 90 | .70783E−02 | .99296E+00 |
| 41 | .15560E−01 | .98465E+00 | 91 | .70005E−02 | .99304E+00 |
| 42 | .15189E−01 | .98501E+00 | 92 | .69243E−02 | .99312E+00 |
| 43 | .14834E−01 | .98535E+00 | 93 | .68498E−02 | .99319E+00 |
| 44 | .14496E−01 | .98568E+00 | 94 | .67768E−02 | .99326E+00 |
| 45 | .14173E−01 | .98600E+00 | 95 | .67054E−02 | .99333E+00 |
| 46 | .13864E−01 | .98630E+00 | 96 | .66355E−02 | .99340E+00 |
| 47 | .13569E−01 | .98659E+00 | 97 | .65671E−02 | .99347E+00 |
| 48 | .13285E−01 | .98687E+00 | 98 | .65000E−02 | .99354E+00 |
| 49 | .13014E−01 | .98713E+00 | 99 | .64343E−02 | .99360E+00 |
| 50 | .12753E−01 | .98739E+00 | 100 | .63699E−02 | .99366E+00 |

The immediate question which arises in examining Equation (2.7) is how many terms of the sum have to be included in the computation of the value of $\mu_o$ in order to perform the reconstruction within a given error. In other words, how far from $O_r$ has the body section to be scanned over the sequence of circular orbits to reconstruct the distribution of $\mu$ in a limited region around $O_r$? The answer to this question largely depends upon the dynamic range of values of $\beta_j$. Assume, for example, that the distribution of values of $\beta_j$ is not far from uniform (as it would be approximately in the case of a water filled compensation bag enclosing the body under scrutiny). The contribution of the terms outside of the range $j=\bar{j}$ would be $$\sum_{\bar{j}}^\infty \frac{K_j}{j} \beta_j \sim \frac{2}{\pi} <\beta_j> \frac{1}{\bar{j}} \quad (2.11)$$

As a consequence of this slow rate of decrease with $\bar{j}$ it is apparent that, with the values of $r_1$ in the millimeter range, both scanning and computation must include almost the entire body section if the error in the reconstruction has to be maintained within a small limit, for example, 1%.

PARTIAL SCANNING

The result expressed by Equation (2.11) is equivalent to saying that the contribution of the scanning of an area of the body section located at a distance r from $O_r$ affects the computation of $\mu_o$ as $r^{-1}$. Thus, if one computes the differences of the values of $\mu$ at two points close to each other, the scanning of a surrounding area affects the difference of $\mu$ as $$1/r_1 - 1/r_2 \qquad (2.12)$$

where $r_1$, $r_2$ are the distance of the area from the two points. Thus, for large values of $r_1$, $r_2$ the scanning of an area of the body section affects the differences of values of $\mu$ essentially as $r_{1,2}^{-2}$. By using a differential-like method in the image reconstruction, it is possible to confine both scanning and computation to a limited area of the body section. As one example of a mathematical analysis of this method, consider first the average value of $\mu$ within a circle of radius $lr$. The average $<\mu>$ is given by $$<\mu> = \frac{1}{l^2} \sum_{h=0}^{l-1} [(h+1)^2 - h^2] \mu_h \qquad (2.13)$$

By virtue of Equation (2.5), Equation (2.13) transforms to $$<\mu> = \frac{1}{4\pi r_1} \frac{1}{l^2} \int_0^{2\pi} \left[ \sum_{j=0}^{l-1} \frac{\overline{K}_j}{j} \beta_j - \sum_{j=l}^{\infty} \frac{\overline{K}_{o,j}}{j} \beta_j \right] d\psi \qquad (2.14)$$

where $$\overline{K}_j = \frac{1}{\theta_{j,1}} [2j - \theta_{1,j-1}\overline{K}_1 - \theta_{2,j-1}\overline{K}_2 - \ldots - \theta_{j-1,2}\overline{K}_{j-1}] \qquad (2.15)$$

$$\overline{K}_1 = \frac{2}{\theta_{1,1}} = \frac{2}{\sqrt{3}}$$

$$\overline{K}_{o,j} = \frac{1}{\theta_{j,1}} [\psi_j - \theta_{1,j-l+1}\overline{K}_{o,l} - \theta_{l-1,j-l}\overline{K}_{o,l-1} - \ldots - \theta_{j-1,2}\overline{K}_{o,j-1}]$$

$$\psi_j = 1 + \theta_{1,j}\overline{K}_1 + \theta_{2,j-1}\overline{K}_2 + \ldots + \theta_{l-1,j-l+2}\overline{K}_{l-1}$$

The coefficients $K_j$ in Equation (2.7) and $\overline{K}HD$ o,j in Equation (2.14) satisfy the asymptotic condition $$\lim_{j \to \infty} (j\overline{K}_{o,j}) = l^2 \lim_{j \to \infty} (j K_j) \qquad (2.16)$$

Thus, from Equations (2.7) and (2.14) one obtains $$\mu_o - <\mu> = \qquad (2.17)$$

$$\frac{1}{4\pi r_1} \int_0^{2\pi} \left[ \left(1 - \frac{1}{l^2}\right) \beta_o - \sum_{j=1}^{l-1} \phi_{i,j}\beta_j - \sum_{j=l}^{\infty} \phi_{e,j}\beta_j \right] d\psi$$

where $$\phi_{i,j} = \frac{1}{j}\left[K_j + \frac{1}{l^2}\overline{K}_j\right] \; ; \; \phi_{e,j} = \frac{1}{j}\left[K_j - \frac{1}{l^2}\overline{K}_{o,j}\right] \qquad (2.18)$$

Asymptotically the coefficient $\phi_{e,j}$ decreases as $j^{-4}$ and this rapid rate of decay is the basis for a localized scanning and image reconstruction.

An important property of both equations (2.7) and (2.17) is the uniform averaging process of the attenuation measurements over each circle of the image reconstruction sequence, as a result of the integration over $2\pi$. Thus, the effect of the statistical fluctuations of the individual measurements of $\beta$ is minimized uniformly over the entire reconstruction area.

Both Equations (2.7) and (2.17) provide the solution of the reconstruction problem. The reconstruction point $O_r$ is an arbitrary point in the x, y plane and Equations (2.7) and (2.17) assume that the values of the attenuation data $\beta$ have been measured over the family of circles concentric with $O_r$. Assume that the attenuation measurements have been conducted in the polar system of coordinates $\rho$, $\psi$ of FIG. 9 in such a way that the values of $\beta$ are known over the family of circles concentric with the origin O. From Equation (2.7), the value of $\mu$ at a point $O_r$ of polar coordinates $r,\theta$ is given by $$\mu(r,\theta) = \frac{1}{4\pi r_1} \int_0^{2\pi} \Big\{ \beta[r\cos(\psi - \theta),\psi] - \qquad (2.19)$$

$$\sum_1^{\infty} \frac{K_j}{j} \beta[r\cos(\psi - \theta) + jr_1,\psi] \Big\} d\psi$$

Figure 9:
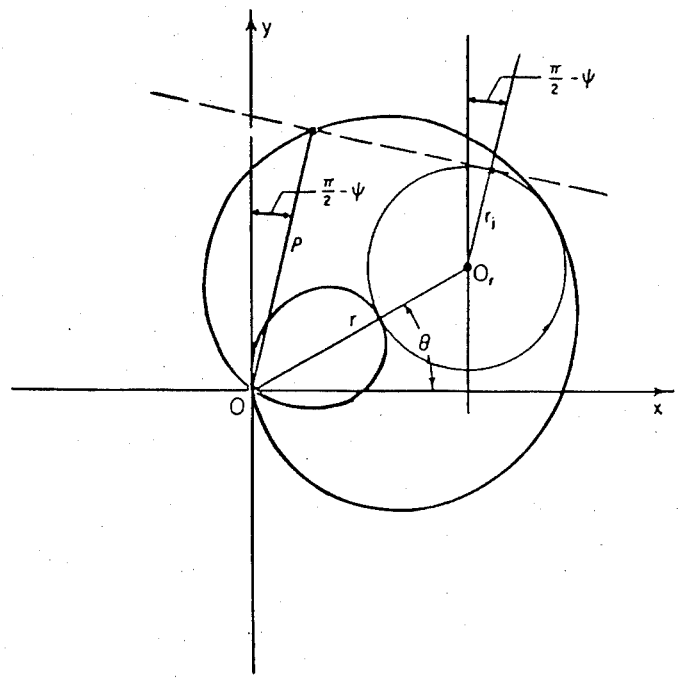
FIG. 9 shows a change of coordinates between scanning and reconstruction frames of references.

FIG. 9 shows the locus of the points of tangence of the circles of center O with the X-ray beams which are located at a distance $r_j = jr_1$ from the reconstruction point $O_r$. From Equation (2.17) the value of $\mu - <\mu>$ at $O_r$ is $$\mu - <\mu> = \frac{1}{4\pi r_1} \int_0^{2\pi} \Big\{ \left(1 - \frac{1}{l^2}\right) \beta[r\cos(\psi - \theta),\psi] - \qquad (2.20)$$

$$\sum_i^{\infty} \phi_j \beta[r\cos(\psi - \theta) + jr_1,\psi] \Big\} d\psi$$

where $$\phi_j = \phi_{i,j}, j \leq l - 1 \qquad (2.21)$$

$$\phi_j = \phi_{e,j}, j \geq l$$

Both equations (2.19) and (2.20) can be written in the same form of the reconstruction solution obtained with a convolution approach. Consider the function $$f(hr_1,\psi) = \sum_{j=0}^{\infty} F_j\{\beta[(h+j)r_1,\psi] + \beta[(h-j)r_1,\psi]\} \qquad (2.22)$$

where the coefficients $F_j$ are $$F_j = \begin{cases} 1 & j = 0 \\ -\dfrac{K_j}{j} & j \neq 0 \end{cases} \qquad (2.23)$$

Coefficients $F_j$ are the weighting functions and they satisfy the condition $$\sum_{j=0}^{\infty} F_j = 0 \qquad (2.24)$$

In Equation (b 2.22) one has $$\beta](h-j)\,r_1\psi] = \beta[|(h-j)\,r_1|,\,\psi+\pi] \qquad (2.25)$$

when $$h-j<0 \qquad (2.26)$$

Equation (2.19) transforms to $$\mu(r,\theta) = \frac{1}{4\pi r_1} \int_0^\pi f[|r\cos(\psi - \theta)|,\psi]d\psi \qquad (2.27)$$

Figure 10:
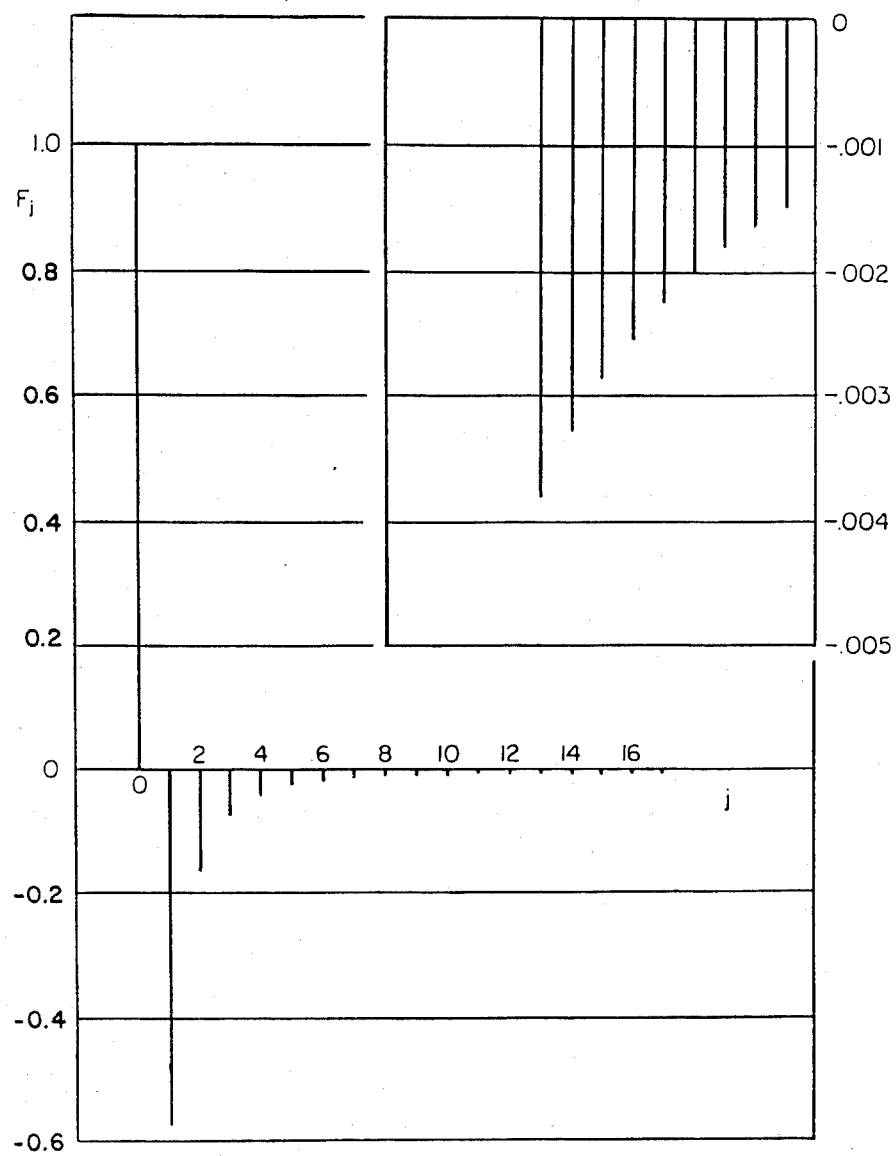
FIG. 10 is a plotting of the values of $F_j$.

The coefficients $F_j$ are plotted in FIG. 10 and the numerical values of $F_j$ are given in the Table II for $J \leq 100$.

TABLE II

| j | $-F_j$ | j | $-F_j$ |
|---|---|---|---|
| 1 | .57735E+00 | 51 | .24514E−03 |
| 2 | .16413E+00 | 52 | .23579E−03 |
| 3 | .73842E−01 | 53 | .22697E−03 |
| 4 | .41355E−01 | 54 | .21863E−03 |
| 5 | .26306E−01 | 55 | .21075E−03 |
| 6 | .18172E−01 | 56 | .20328E−03 |
| 7 | .13295E−01 | 57 | .19620E−03 |
| 8 | .10145E−01 | 58 | .18949E−03 |
| 9 | .79948E−02 | 59 | .18311E−03 |
| 10 | .64621E−02 | 60 | .17706E−03 |
| 11 | .53313E−02 | 61 | .17129E−03 |
| 12 | .44734E−02 | 62 | .16581E−03 |
| 13 | .38071E−02 | 63 | .16058E−03 |
| 14 | .32794E−02 | 64 | .15560E−03 |
| 15 | .28543E−02 | 65 | .15084E−03 |
| 16 | .25068E−02 | 66 | .14630E−03 |
| 17 | .22191E−02 | 67 | .14197E−03 |
| 18 | .19783E−02 | 68 | .13782E−03 |
| 19 | .17747E−02 | 69 | .13385E−03 |
| 20 | .16009E−02 | 70 | .13005E−03 |
| 21 | .14515E−02 | 71 | .12641E−03 |
| 22 | .13221E−02 | 72 | .12292E−03 |
| 23 | .12093E−02 | 73 | .11957E−03 |
| 24 | .11103E−02 | 74 | .11636E−03 |
| 25 | .10230E−02 | 75 | .11328E−03 |
| 26 | .94559E−03 | 76 | .11031E−03 |
| 27 | .87665E−03 | 77 | .10747E−03 |
| 28 | .81500E−03 | 78 | .10473E−03 |
| 29 | .75692E−03 | 79 | .10209E−03 |
| 30 | .70971E−03 | 80 | .99552E−04 |
| 31 | .66456E−03 | 81 | .97107E−04 |
| 32 | .62359E−03 | 82 | .94752E−04 |
| 33 | .58629E−03 | 83 | .92481E−04 |
| 34 | .55224E−03 | 84 | .90291E−04 |
| 35 | .52108E−03 | 85 | .88178E−04 |
| 36 | .49248E−03 | 86 | .86138E−04 |
| 37 | .46617E−03 | 87 | .84169E−04 |
| 38 | .44192E−03 | 88 | .82266E−04 |
| 39 | .41951E−03 | 89 | .80426E−04 |
| 40 | .39876E−03 | 90 | .78648E−04 |
| 41 | .37952E−03 | 91 | .76928E−04 |
| 42 | .36164E−03 | 92 | .75264E−04 |
| 43 | .34499E−03 | 93 | .73654E−04 |
| 44 | .32946E−03 | 94 | .72094E−04 |
| 45 | .31496E−03 | 95 | .70584E−04 |
| 46 | .30140E−03 | 96 | .69120E−04 |
| 47 | .28870E−03 | 97 | .67702E−04 |
| 48 | .27678E−03 | 98 | .66327E−04 |
| 49 | .26558E−03 | 99 | .64993E−04 |
| 50 | .25505E−03 | 100 | .63699E−04 |

In a similar manner Equation (2.20) can be written again with the definition of the function $$g(hr_1,\psi) = \sum_{j=0}^{\infty} G_j\{\beta[(h + j)r_1,\psi] + \beta[(h - j)r_1,\psi]\} \qquad (2.28)$$

where $$G_j = \begin{cases} 1 - \dfrac{1}{j^2} & j = 0 \\ -\phi_j & j \neq 0 \end{cases} \qquad (2.29)$$

and the following condition is satisfied $$\sum_{j=0}^{\infty} G_j = 0 \qquad (2.30)$$

Figure 11:
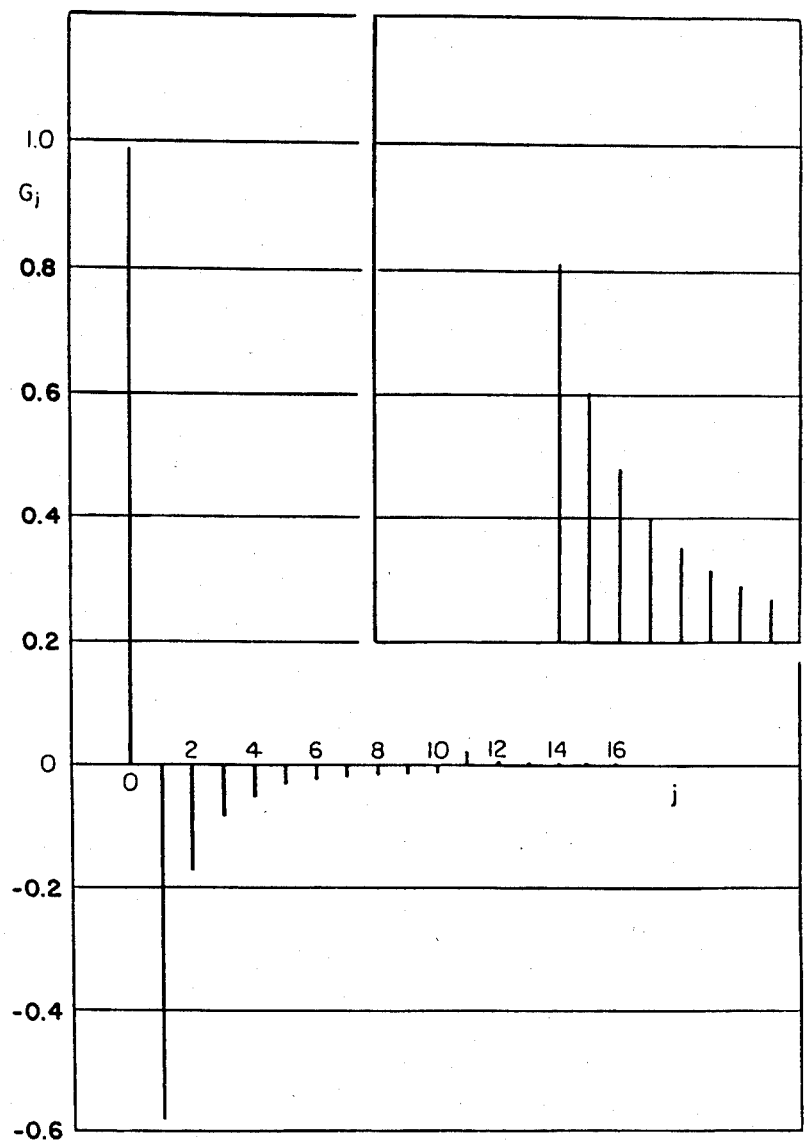
FIG. 11 is a plotting of the values of $G_j$.

A plotting of $G_j$ is shown in FIG. 11 and the values of $G_j$ are given in Table III for $j<100$ in the particular case of $l=11$. One observes the inversion of sign of the terms $G_j$ for $i>1$.

TABLE III

| j | $+G_j$ | j | $+G_j$ |
|---|---|---|---|
| 1 | −.58689E+00 | 51 | .86350E−05 |
| 2 | −.17424E+00 | 52 | .79768E−05 |
| 3 | −.84126E−01 | 53 | .73804E−05 |
| 4 | −.51720E−01 | 54 | .68389E−05 |
| 5 | −.36715E−01 | 55 | .63463E−05 |
| 6 | −.28608E−01 | 56 | .58975E−05 |
| 7 | −.23748E−01 | 57 | .54877E−05 |
| 8 | −.20611E−01 | 58 | .51130E−05 |
| 9 | −.18470E−01 | 59 | .47699E−05 |
| 10 | −.16944E−01 | 60 | .44551E−05 |
| 11 | .23816E−01 | 61 | .41660E−05 |
| 12 | .94539E−02 | 62 | .39000E−05 |
| 13 | .50385E−02 | 63 | .36549E−05 |
| 14 | .30838E−02 | 64 | .34288E−05 |
| 15 | .20470E−02 | 65 | .32200E−05 |
| 16 | .14342E−02 | 66 | .30269E−05 |
| 17 | .10449E−02 | 67 | .28481E−05 |
| 18 | .78441E−03 | 68 | .26823E−05 |
| 19 | .60305E−03 | 69 | .25284E−05 |
| 20 | .47279E−03 | 70 | .23855E−05 |
| 21 | .37682E−03 | 71 | .22525E−05 |
| 22 | .30460E−03 | 72 | .21286E−05 |
| 23 | .24925E−03 | 73 | .20132E−05 |
| 24 | .20616E−03 | 74 | .19055E−05 |
| 25 | .17216E−03 | 75 | .18050E−05 |
| 26 | .14500E−03 | 76 | .17110E−05 |
| 27 | .12307E−03 | 77 | .16230E−05 |
| 28 | .10519E−03 | 78 | .15406E−05 |
| 29 | .90485E−04 | 79 | .14634E−05 |
| 30 | .78291E−04 | 80 | .13910E−05 |
| 31 | .68105E−04 | 81 | .13230E−05 |
| 32 | .54541E−04 | 82 | .12591E−05 |
| 33 | .52293E−04 | 83 | .11991E−05 |
| 34 | .46126E−04 | 84 | .11426E−05 |
| 35 | .40849E−04 | 85 | .10893E−05 |
| 36 | .36311E−04 | 86 | .10392E−05 |
| 37 | .32391E−04 | 87 | .99189E−06 |
| 38 | .28990E−04 | 88 | .94726E−06 |
| 39 | .26027E−04 | 89 | .90511E−06 |
| 40 | .23435E−04 | 90 | .86528E−06 |

TABLE III-continued

| j | +G_j | j | +G_j |
|---|------|---|------|
| 41 | .21160E−04 | 91 | .82762E−06 |
| 42 | .19155E−04 | 92 | .79200E−06 |
| 43 | .17384E−04 | 93 | .75827E−06 |
| 44 | .15814E−04 | 94 | .72631E−06 |
| 45 | .14419E−04 | 95 | .69603E−06 |
| 46 | .13174E−04 | 96 | .66731E−06 |
| 47 | .12062E−04 | 97 | .64006E−06 |
| 48 | .11065E−04 | 98 | .61418E−06 |
| 49 | .10169E−04 | 99 | .58961E−06 |
| 50 | .96627E−05 | 100 | .56625E−06 |

In a way similar to Equation (2.11) one can compute in Equation (2.28) the order of magnitude of the contribution of the terms of the sum outside of j=j with the assumption of a quasi-uniform distribution of values of $\beta_j$. One has $$\sum_{j}^{\infty} G_j \{\beta[(h-j)r_i,\psi] + \beta[(h-j)r_i,\psi]\} \sim <\beta> \frac{4}{3\pi} \frac{(l-1)^2}{j^3} \quad (2.31)$$

Equation (2.17) can be written again in the form $$(\mu - <\mu>)_{r,\theta} = \frac{1}{4\pi r_1} \int_o^\pi g[|r\cos(\psi - \theta)|,\psi]d\psi \quad (2.32)$$

By virtue of Equations (2.18), Equation (2.32) reduces to Equation (2.27) in the limit $1 \rightarrow \sqrt{} =$. Thus Equation (2.32) may be considered a more general solution of the reconstruction Equation (2.32) defines the approach of the localized scanning. Due to the rapidly diminishing value of the contribution of the terms of the second sum in Equation (2.17), a progressively larger error in the measurement of $\beta$ can be tolerated for increasing values of j (i.e. for increasing distance from the region of reconstruction of the $\Delta\mu$image). Beyond a given distance the measurement of $\beta$ becomes unnecessary and assumed $\beta$ values can be substituted for the actual measured data without introducing a significant error in the calculation of $\Delta\mu$.

In the limit of radius of l approaching unity, the reconstructed value $\Delta\mu$ acquires the property of the local average of the second derivative of $\mu$. This is illustrated in FIG. 3 which shows the value of $\Delta\mu$ as a function of the distance from a plane interface M between two uniform media. The value of $\Delta\mu$ is zero at the interface and at a large distance from the interface. Finite values of $\Delta\mu$ are confined to the region $+$ or $-lr_1$ from the interface.

Thus the relationship between a $\Delta\mu$ image and a $\mu$ image is controlled by the relation of the parameter l.

If one has to extract the local value of $\mu$ from the $\Delta\mu$ image an independent knowledge or measurement of the value of $\mu$ within each radius l $r_1$ is required. This average may be is known beforehand or it may be obtained from a total scanning of the body section. However, the latter need only have a low spatial resolution if l is large compared to unity and, as a consequence, the total scanning has less stringent requirements on the stability of the attenuation measurements as compared to a high spatial resolution scanning.

Two categories of clinical intentions can be identified where, in principal, the $\Delta\mu$ image is of diagnostic value per se.

If the images are used to diagnose localized density perturbations in essentially uniform areas (the liver is an example) and the value of l is such that the perturbations fit well within the averaging circle, the information contained in the $\Delta\mu$ image provides the full diagnosis of the anomaly or departure from usual tissue properties. A scanning localized to the area of interest provides the set of $\beta$ measurements required for the $\Delta\mu$ image. The precision of the reconstruction is placed in the difference between local and normal values $\mu$ rather than the absolute values of $\mu$.

Figure 13:
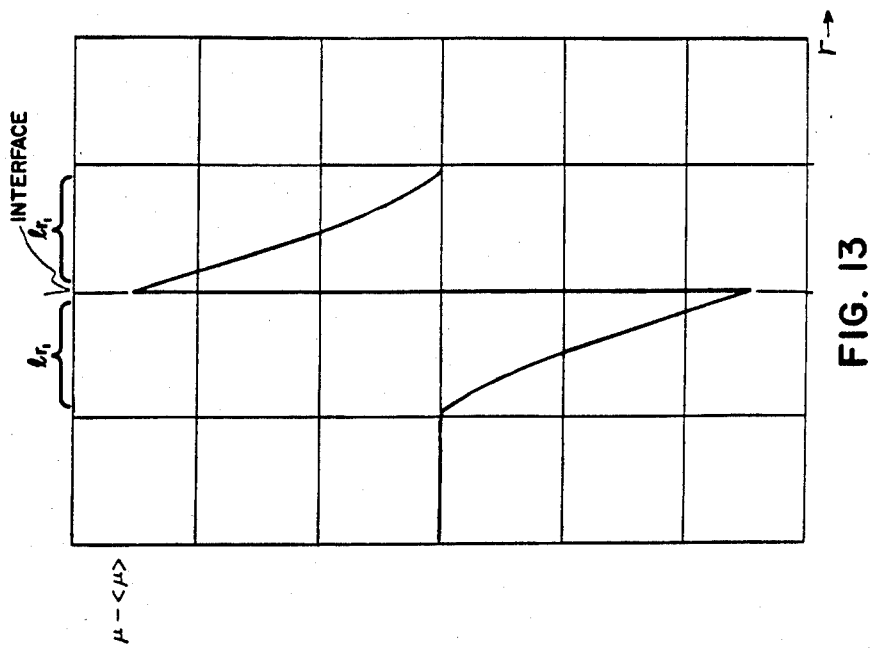
FIG. 13 is a poltting of the value of $\mu - <\mu>$ across a plane interface between uniform media.

The second category corresponds to images of the interface of body organs and boundaries of tissue anomolies. These images correspond to small values of l, for example l=2, where the boundaries are identified by a distribution of positive and negative values of $\Delta\mu$ as shown in FIG. 13 (as long as the radius of curvature of the boundary is larger than several pixal sizes).

EFFECTS OF SCANNING PROCEDURE ON IMAGE RECONSTRUCTION

To compute either function $g(hr_1,\psi)$ or $f(hr_1,\psi)$, it is necessary to extract the values of $\beta$ from the measurements of the X-ray beam intensity according to Equation (2.1). In an actual scanning and reconstruction procedure the values of $I_o$ and $I_e$ in Equation 2(1) are measured at the entrance and exit of the body section respectively. At a first glance it would then appear that the reconstruction calculation is dependent upon the values of intensity $I_o$ outside of the body. However, it is easy to write solutions of $\mu$ and $\mu-<\mu>$ in a form which shows that a knowledge of $I_o$ is not required. To do so, write $f(hr_1, \psi)$ in the form $$f(hr_1,\psi) = \sum_{j=-\infty}^{+\infty} \tilde{F}_j \beta[(h+j)r_1,\psi] \quad (3.1)$$

where $$\begin{cases} \tilde{F}_{-j} = \tilde{F}_{+j} = F_{|j|} \; (j \neq 0) \\ \tilde{F}_o = 2F_o \end{cases} \quad (3.2)$$

By virtue of 2.24, $\tilde{F}_j$ satisfies the condition $$\sum_{-\infty}^{+\infty} \tilde{F}_j = 0 \quad (3.3)$$

Consequently in Equation (3.1), the value of f does not change is the values of $\beta$ are changed into a new distribution $\beta'$ such that $$\beta'[(h+j)r_1, \psi]=\beta[(h+j)r_1, \psi]+\beta_o(\psi) \quad (3.4)$$

where $\beta_o$ is an arbitrary constant independent of j. In a similar way $g(hr_1, \psi)$ can be written as $$g(hr_1,\psi) = \sum_{j=-\infty}^{+\infty} \tilde{G}_j \beta[(h+j)r_1,\psi] \quad (3.5)$$

where $$\begin{cases} \tilde{G}_{-j} = \tilde{G}_{+j} = G_{|j|} & (j \neq 0) \\ \tilde{G}_o = 2\left(1 - \frac{1}{l^2}\right) & (j = 0) \end{cases} \quad (3.6)$$

$\tilde{G}_j$ also satisfies the condition $$\sum_{-\infty}^{+\infty} \tilde{G}_j = 0 \quad (3.7)$$

Thus g (hr$_1$, $\psi$) is also independent of an additive arbitrary constant $\beta_o$ in the values of the attenuation measurements.

ARTIFACTS GENERATED BY PARTIAL SCANNING

In the case of a partial scanning, the attenuation data are collected only within a circle of radius $r_s$, resulting in an error in the reconstruction of either $\mu$ or $\mu - <\mu>$. This error is essentially due to the superposition of artifacts generated by the incomplete scanning of points located outside of the circle of radius $r_s$.

Figure 14:
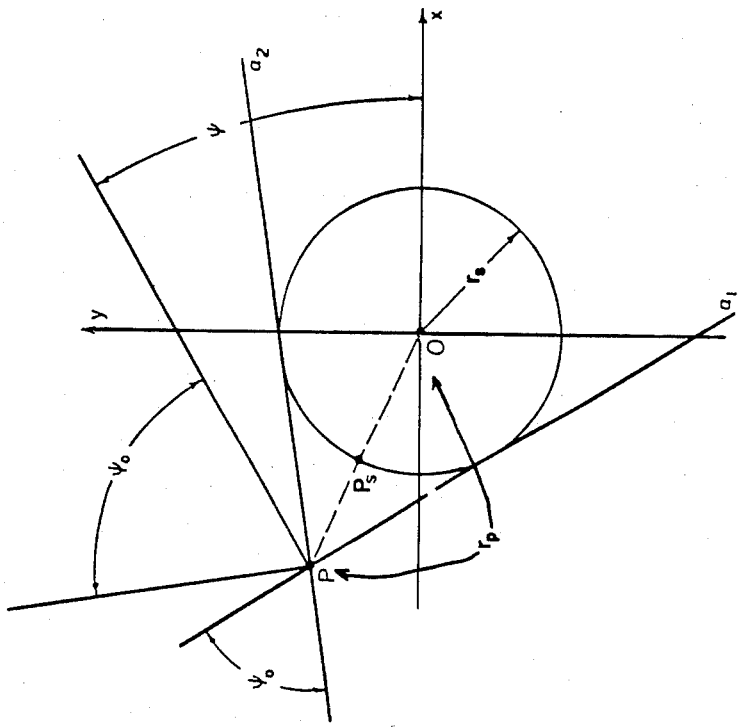
FIG. 14 is a partial scanning procedure.

Assume a $\delta$-like object located at a point P at a distance $r_p > r_s$ as shown in FIG. 14 and reconstruct the value of either $\mu$ or $\mu - <\mu>$ within the circle of radius $r_s$ with no other object in the scanning plane.

If the distance of each scanning ray from the center 0 never exceed $r_s$, the attenuation data are collected between the angles $\psi$, $\psi + \psi_o$ formed by the two lines which are perpendicular to the tangents $a_1$, $a_2$ from P to the circle of radius $r_s$ as shown in FIG. 14. Thus point P is scanned only within the fraction $\psi_o/\pi$ of the total scanning cycle, regardless of the scanning procedure. Accordingly the presence of the $\delta$-object outside of the scanning circle generates an artifact distribution which is essentially oriented along the two lines $a_1$ and $a_2$. In the limit of $r_p \to r_s$, i.e., for p approaching the point $P_s$ on the scanning circle, one has $\psi_o \to \pi$ and the two lines $a_1$, $a_2$ coverage in a single line at $P_s$ tangent to the circle.

As a consequence the partial scanning introduces an error in the image reconstruction within the circle of radius $r_s$, which depends primarily upon the distance of the reconstruction point from the lines $a_1$, $a_2$ rather than the distance from the location P of the object left outside of the scanning circle. Hence the maximum error is found close to the points of tangence of $a_1$, $a_2$ with the circle.

The reconstructed value of $\mu$ within a region of the scanning circle close to either $a_1$, or $a_2$, is described by an approximate solution written in the form:

$$\mu(r,\theta) \sim \frac{\beta}{4\pi \bar{r}} \sum_{-j_2}^{+j_1} \frac{\tilde{F}_j}{\sqrt{1 - j^2 \left(\frac{r_1}{\bar{r}}\right)^2}} \quad (4.1)$$

where $\bar{r}$ is the distance of the reconstruction point from P and $j_1$, $j_2$ are given by $$j_1 \sim \frac{\bar{r}}{r_1} |\sin \eta|; j_2 \sim \frac{\bar{r}}{r_1} |\sin(\eta - \psi_o)| \quad (4.2)$$

Figure 15:
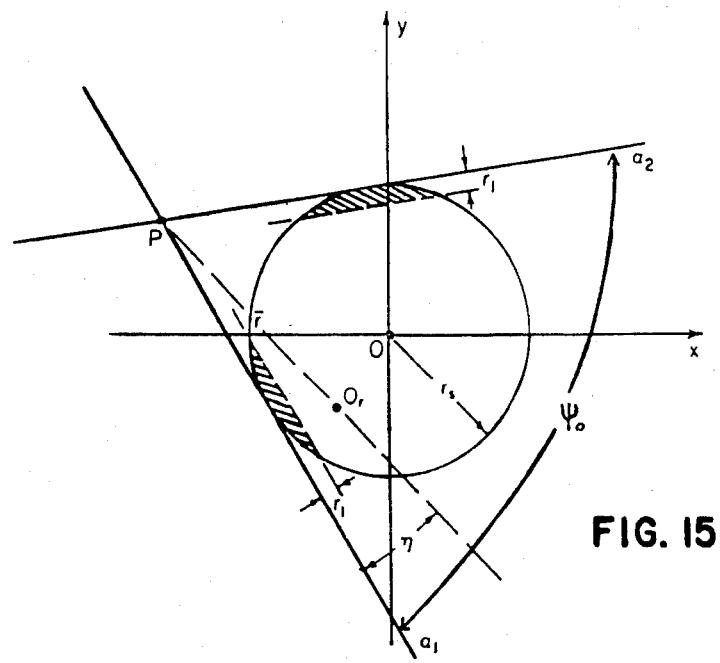
FIG. 15 illustrates the geometry of artifacts generated in a partial scanning approach.

$\eta$ being the angle between $a_1$ and the line PO$_r$ as shown in FIG. 15. The value of $\mu - <\mu>$ at the same point is obtained simply by substituting $\mu - <\mu>$ to $\mu$ and $\tilde{G}_j$ to $\tilde{F}_j$ in Equation (4.1), i.e.

$$\mu - <\mu> \sim \frac{\beta}{4\pi \bar{r}} \sum_{-j_2}^{+j_1} \frac{\tilde{G}_j}{\sqrt{1 - j^2 \left(\frac{r_1}{\bar{r}}\right)^2}} \quad (4.3)$$

The maximum values of both $\mu$ and $\mu - <\mu>$ are found within a distance from $a_1$, $a_2$ of the order of $r_1$, and the order of magnitude of the maxima are $$\mu_{max} \sim \frac{\beta}{2\pi \bar{r}} ; (\mu - <\mu>)_{max} \sim \frac{\beta}{2\pi \bar{r}}\left(1 - \frac{1}{l^2}\right) \quad (4.4)$$

Thus the two maxima are of the same order of magnitude regardless of the value of the parameter l, and decrease slowly with the distance of P from the points of tangence. As indicated by the shaded regions of FIG. 15, only a small fraction of the circle area, close to the periphery of the scanning circle is affected by the maximum amplitude of the artifacts given by Equations (4.4).

As the distance from either $a_1$ or $a_2$ increases, the reconstructed value of $\mu$ decreases rather rapidly. For values of $\eta$ close to 0 and $\psi_0$ and in the intervals $$\eta >> \frac{r_1}{\bar{r}} ; \psi_0 - \eta >> \frac{r_1}{\bar{r}} \quad (4.5)$$

the value $\mu$ is $$\mu \sim \frac{\beta \, r_1}{2\pi^2} \frac{1}{\bar{r}^2 \, \alpha_{1,2}} \quad (4.6)$$

where $$\alpha_1 = \eta; \alpha_2 = \psi_0 - \eta \quad (4.7)$$

Figure 16:
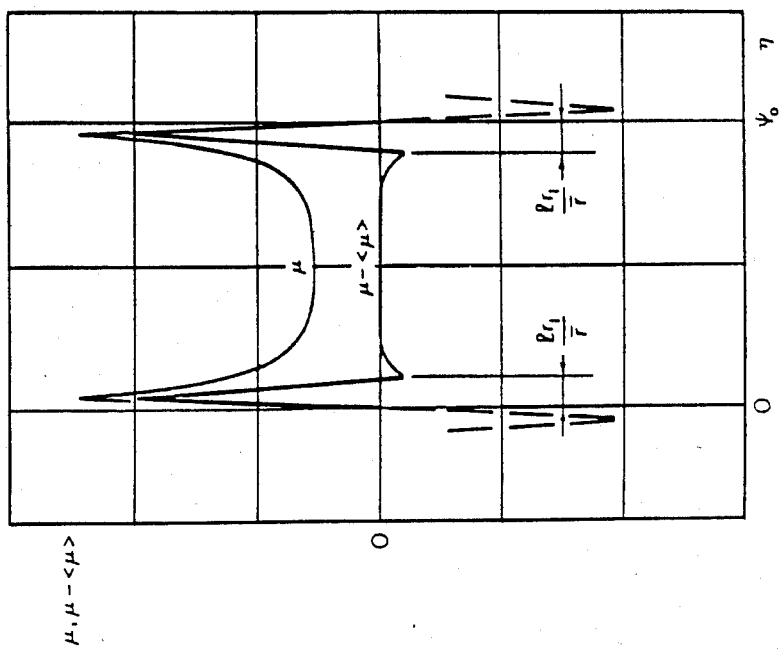
FIG. 16 is a plotting of the values of $\mu$ and $\mu - <\mu>$ within a partial scan region.

$\mu - <\mu>$ decreases also and attains a negative value at values of $\eta$ whose order of magnitude is given by $$\eta \sim \psi_0 - \eta \sim \frac{lr_1}{\bar{r}}, \quad (4.8)$$

and for values of $\eta$ $$\frac{lr_1}{\bar{r}} < \eta < \psi_0 - \frac{lr_1}{\bar{r}} \quad (4.9)$$

the magnitude of $\mu - <\mu>$ decreases very rapidly with either $\alpha_1$ or $\alpha_2$ according to the equation $$\mu - <\mu> \sim - \frac{\beta r_1^3}{3\pi^2} \frac{(l-1)^2}{\bar{r}^4 \, \alpha_{1,2}^3} \quad (4.10)$$

i.e., the magnitude of $\mu - <\mu>$ decreases inversely to the third power of the distance from either $a_1$, $a_2$. As a consequence, within a distance $lr_1$ from the periphery of the circle the $\Delta\mu$ image reconstruction is virtually unaffected by the presence of the $\delta$-object outside of the scanning circle. A plotting of both $\mu$ and $\mu - <\mu>$ within the angular interval $\psi_o$ is shown in FIG. 16.

RECONSTRUCTION COMPUTATION

The image reconstruction will, in general, be implemented numerically in a general purpose digital computer which may, additionally, include dedicated array processing hardware. The specific solutions are, of course, highly dependent on such factors as the required computational speed, accuracy, and capital investment. The following discussions is, therefore, intended to enable those skilled in the computer programming art to effectively implement numerical solutions without undue experimentation.

The general solution to the reconstruction problem is stated by Equation (2.32), since in the limit $1 \to \infty$, $<\mu> \to 0$ and $G_j \to F_j$ which are the weighting functions for reconstruction of $\mu$. Numerical implementation of the reconstruction algorithm can be discussed in terms of Equations (2.28), (2.29) and (2.32), recognizing that Equations (2.22), (2.23) and (2.27) are recovered as a special case. Therefore, the differences between a partial scanning and reconstruction and a total scanning and reconstruction reside in the magnitude of the requirements for information storage, reconstruction speed, and interpretation of the solution, but not in the form of the equations or the logic of the instructions to implement their solution. Accordingly, a single reconstruction code may be developed in which specification of the value 1 is the only parameter which distinguishes a "partial reconstruction", producing the solution for $\mu - <\mu>$, from a "total reconstruction", producing the solution for $\mu$.

The reconstruction code may be structured in four basic modules. The first module calculates and stores the weighting functions (Equations 2.23 and 2.29);

$$\alpha_j = \begin{cases} F_j & \text{if } l \geq j\,\text{max} \\ G_j & \text{if } l < j\,\text{max} \end{cases} \quad (j = 0, 1, 2, \ldots j_{max}) \quad (5.1)$$

and an auxiliary function;

$$\gamma_j = \sum_{k=j}^{j_{max}} \alpha_k (j = 1, 2, 3, \ldots j_{max}) \quad (5.2)$$

Selection of the value of $j_{max}$ must be made on the basis of accuracy and computational speed; these considerations will be elaborated in the following discussion.

Figure 12:
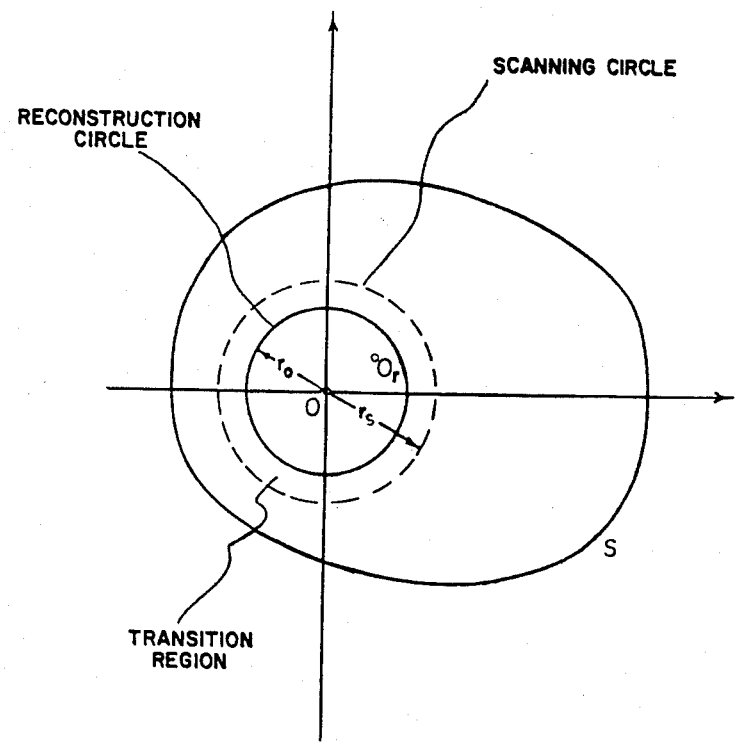
FIG. 12 defines a scan transition region.

The second module of the reconstruction code calculates the function f or g (depending of the value of l) in accord with Equations (2.22) or (2.28):

$$\begin{Bmatrix} f(hr_1, \psi) \\ g(hr_1, \psi) \end{Bmatrix} = \quad (5.3)$$

$$\sum_{j=0}^{j_s-h} \alpha_j \beta[(h+j)r_1, \psi] + \sum_{j=0}^{j_s+h} \alpha_j \beta[|h+j|r_1, \psi+\pi] +$$

$$\beta_{0,1}(\psi)\gamma(j_s - h + 1) + \beta_{0,2}(\psi)\gamma(j_s + h + 1)$$

$$(h = -j_o, 1-j_o, 2-j_o, \ldots -1, 0, 1, \ldots j_o-2, j_o-1, j_o)$$

where the scanning is carried out over a maximum radius $r_s = j_s r_1$ and the reconstruction is to be carried out within a circle of radius $r_o = j_o r$. The values of $\beta(r, \psi)$ may be obtained from direct measurement as provided in prior art scanning instrumentation. The functions $\beta_{0,1}(\psi)$ and $\beta_{0,1}(\psi)$ represent either (a) the background attenuation measured outside the body in the case of a total scanning i.e., $\beta_{0,1} = \beta_{0,2} = \beta_0(\psi)$, or (b) suitable approximations to the attenuation in the compensation region (see FIG. 12) in the case of a partial scanning, e.g., $\beta_{0,1} = \beta(r_s, \psi)$ and $\beta_{0,2} = \beta(r_s, \psi + \pi)$. The transformation stated by Equations (2.25) and (2.26) should be recalled in connection with Equation (5.3).

If the values of $\beta$ are reasonably uniform, the value of $j_{max}$ required to achieve a specified degree of accuracy can be estimated form Equation (2.30) or (2.24). The error $\epsilon$ incurred by truncating the summation after $j_{max}$ terms is simply $$\sum_{j=0}^{j_{max}} \alpha_j.$$

Thus, $\epsilon \to \infty$ however, as will be demonstrated below, an "exact" solution, in the sense that $$\sum_{j_{max}+1}^{\infty} \alpha_j \beta[(h \pm j)r_1, \psi] = 0,$$

can be achieved with a finite value of $j_{max}$, dictated only by $j_s$ and l.

It can be seen from Equation (5.3) that $j_{max} = j_s + j_o$ is required to complete the indicated summation in this equation. Consider first the case of a total scanning of the body section; $j_o = j_s$ is usual in this case. As pointed out above, an arbitrary constant $\beta_o(\psi)$, may be added to or substracted from the measured attenuation values without affecting the solution for $f(r, \psi)$ (assuming $j_{max} \to \infty$). Therefore, the values of $\beta(r, \psi)$ in Equation (5.3) may be normalized to $\beta(r, \psi) - \beta_o(\psi)$, yielding;

$$f(hr_1, \psi) = \sum_{j=0}^{j_s-h} \alpha_j \beta[((h+j)r_1, \psi) - \beta_o(\psi)] + \quad (5.4)$$

$$\sum_{j=0}^{j_s+h} \alpha_j \beta[(|h-j|r_1, \psi+\pi) - \beta_o(\psi)]$$

in which case the auxiliary function $\gamma_j$ is not needed, and $j_{max} = 2j_s$ is required to complete an "exact" solution. However, for typical values of $j_s$ needed to carry out a total scan of a body section with a high degree of precision, the computational requirement to include $2j_s$ terms in the calculation of $f(fr_1, \psi)$ at each of $2j_s - 1$ radial positions, for each angle $\psi$, may still present an unacceptable limitation on reconstruction speed. On the other hand, use of $j_{max} <$ introduces an error of order $$\sum_{j_{max}+1}^{2j_s}$$

into the solution, which must be assessed in terms of the required precision of the reconstruction.

In the case of a partial scanning, the reconstruction region should be confined to a circle of radius $r_o = r_r - lr_1 = (j_s - l)r_1$. Thus $j_{max} = 2j_s = 1$ is required to carry out the indicated summations in Equation (5.3). If the values of $\beta(r, \psi)$ are normalized with respect to a linear function of r in this case, $$\beta_n(r, \psi) = \beta_{0,1} + (\beta_{0,1} - \beta_{0,2})(r - r_s)/2r_s(-r_s < r < r_s) \quad (5.5)$$

Equation (6.5) becomes:

$$g(hr_1, \psi) = \sum_{j=0}^{j_s-h} a_j[(\beta - \beta_n)(h + j)r_1, \psi)] + \qquad (5.6)$$

$$\sum_{j=0}^{j_s+h} a_j[(\beta - \beta_n)(|h - j|r_1, \psi + \pi)]$$

which only requires $j_{max}=2j_s-1$ terms for an "exact" solution and, again, deletes the auxiliary function $\gamma_j$.

Since the maximum scanning radius $r_s = j_s r$ for a partial scanning is presumably much smaller than that required for a total scanning, the required value of $j_{max}$ for an "exact" solution is correspondingly reduced. Therefore, calculation time for the function g, which is roughly proportional to $j_s^2$, should not be a limiting factor in achievement of acceptable reconstruction speed in the case of a partial reconstruction.

It should be pointed out that since the auxiliary function $\gamma_j$ may be computed, and stored, for arbitrarily large values of $j_{max}$ in the first module of the reconstruction code, at very modest computational expense, Equation (5.3) may be preferred over (5.4) or (5.6), since normalization of the data is not required. Equations (5.4) and (5.6) demonstrate that the minimum number of weighting terms required for exact total and partial reconstruction are $2j_s$ and $2j_s-1$ respectively, if the attenuation values are normalized to $\beta_{0,1} = \beta_{0,2} = 0$.

The third module of the reconstruction code is the "backprojection" or reconstruction step, per se, as given by Equation (2.32) or (2.27):

$$\begin{Bmatrix} \mu(r, \theta) \\ (\mu - <\mu>)(r, \theta) \end{Bmatrix} = \qquad (5.7)$$

$$\frac{1}{4\pi r_1} \int_0^\pi \begin{Bmatrix} f \\ g \end{Bmatrix} (|r\cos(\psi - \theta)|, \psi) d\psi$$

wherein the transformation given by Equations (2.25) and (2.26) has been utilized. The integration may be carried out by the simple trapezoidal rule procedure using equally spaced angular intervals, typically the same as the angular increment in the scanning data. The required values of the integrand are linearly interpolated from the calculated values.

The fourth, and final module of the reconstruction code is the image display. The reconstructed distribution of $\mu$ or $\Delta\mu$ over the scanning plane may be displayed by either (a) assigning a grey scale to the range of values of $\mu$ or $(\mu - <\mu>)$ and a pixel size to each coordinate point $(x, y) = (r\cos\theta, r\sin\theta)$ to produce a photographic type image, or (b) searching the distribution for the contour lines $\mu = $ constant or $(\mu - <\mu>) = $ constant which can be plotted as continuous functions of $(x,y)$ or $(r,\theta)$. Details of both techniques are well known in the art; however, it should be pointed out that generation of a grey scale image is relatively fast and qualitatively informative, whereas the contour line technique provides more quantitative detail, both in terms of spatial and density resolution, but at a much greater computational expense. Obviously, plots of $\mu$ or $\Delta\mu$ as a function of position along selected lines within the scanning plane may also be obtained in place of, or in addition to, the image display.

CORRECTION OF ARTIFACTS DUE TO FINITE SAMPLING

The reconstruction algorithm is based on the assumption that $\mu$ is a continuous function of position which changes slowly over the elemental step $r_1$. Because of the interpolation procedures, artifacts are generated in the presence of discontinuities, such as interfaces between regions with largely different values of $\mu$. Errors and artifacts are also generated by the finite radial and angular sampling intervals of any scan procedure.

Figure 17:
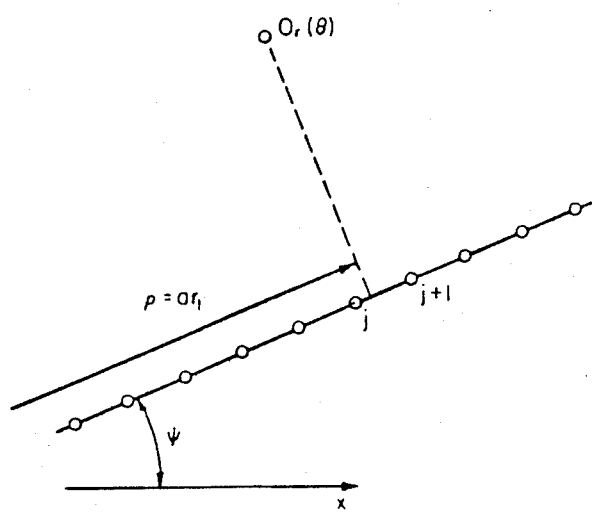
FIG. 17 illustrates the generation of interpolation artifacts during backprojection.

In FIG. 17 $O_r$ is a reconstruction point. During the summation or backprojection of data that numerically replaces the integration in Equation 2.27 some interpolation must be made between proximal values of f, such as $f[jr_1, \psi]$ and $f[(j+1)r_1, \psi]$. Interpolation artifacts will be generated if f suffers a large change in this interval. Specifically the sign inversion of $F_j$ and $G_j$ from a positive value at $j=0$ to negative values at $j=\pm 1$ is responsible for the large interpolation errors in the presence of discontinuities of the distribution of $\mu$. The reconstruction algorithm may be optimized by modifying the weighting functions in such a way as to minimize the interpolation error and the resulting reconstruction noise. A modification of the algorithm leading to a reduction of the computational reconstruction noise will also have a beneficial effect on image artifacts generated by statistical noise in the data acquisition system.

Obviously, any change in the shape of the weighting functions intended to minimize the reconstruction noise must be analyzed in terms of its effect on the reconstructed values of both $\mu$ and $\mu - <\mu>$ and in particular on the spatial resolution of the reconstructed images. To discuss this problem it is convenient to modify the reconstruction approach discussed above by substituting the calculation of $\mu$ at each point $O_r(r,\theta)$ with the calculation of a weighted average $\bar{\mu}$ of the attenuation coefficient as defined by the equation $$\bar{\mu}(r, \theta) = \int_0^{2\pi} d\theta \int_0^\infty \mu(s, \alpha) \, \omega(\bar{r}) \, \bar{r} \, d\bar{r} \qquad (6.1)$$

where $\bar{r}, \bar{\theta}$ are the polar coordinates relative to the reconstruction point $O_r$.

$$s = [\bar{r}^2 + r^2 + 2\bar{r} r\cos(\bar{\theta} - \theta)]^{\frac{1}{2}} \qquad (6.2)$$

$$\frac{\sin(\bar{\theta} - \theta)}{s} = \frac{\sin(\alpha - \theta)}{\bar{r}}$$

and $\omega(\bar{r})$ is a continuous function of the distance $\bar{r}$ from $O_r$, which satisfies the condition $$2\pi \int_0^\infty \omega(\bar{r}) \, \bar{r} \, d\bar{r} = 1 \qquad (6.3)$$

Assume a family of circles concentric with $O_r$ and radii $$r_h = hr_1 \qquad (6.4)$$

Equation (8.1) can be written in the form $$\bar{\mu} = \sum_{h}^{\infty} M_h \mu_h \qquad (6.5)$$

where $\mu_h$ is the average value of $\mu$ between the circles of center $O_r$ and radii $hr_1$ and $(h+1)r_1$, and $$M_h = 2\pi \int_{hr_1}^{(h+1)r_1} \omega(\bar{r})\, \bar{r}\, d\bar{r} \qquad (6.6)$$

In the manner described above, one obtains the average values $\mu_h$ $$\mu_h = \frac{1}{4\pi r_1} \int_0^{2\pi} \left\{ K_{h,h}\beta_h[r\cos(\psi - \theta), \psi] - \sum_{j=h+1}^{\infty} \frac{K_{j,h}}{j} \beta_j[r\cos(\psi - \theta), \psi] \right\} d\psi \qquad (6.7)$$

where the coefficients $K_{j,h}$ are related to the parameters $\theta_{j,k}$ defined in Equation (2.6) by $$K_{h,h} = \frac{1}{\theta_{h,1}} \qquad (6.8)$$

$$K_{j,h} = \frac{1}{\theta_{j,1}} [\theta_{h,j-h+1} K_{h,h} - \ldots - \theta_{j-1,2} K_{j-1,h}]$$

Thus the value of $\mu$ given by Equation (6.5) can be written as $$\mu = \frac{1}{4\pi r_1} \int_0^\pi f[r|\cos(\psi - \theta)|, \psi] d\psi \qquad (6.9)$$

where $$f(hr_1, \psi) = \sum_{-\infty}^{+\infty} r_j \beta[(h+j)r_1, \psi] \qquad (6.10)$$

$$\Gamma_0 = 2M_0 \qquad (6.11)$$

$$\Gamma_1 = \frac{1}{\theta_{1,1}} (M_1 - M_0)$$

$$\Gamma_2 = \frac{1}{2\theta_{2,1}} (M_2 - M_0 - \theta_{1,2}\Gamma_1)$$

$$\ldots$$

$$\Gamma_j = \Gamma_{-j} = \frac{1}{j\theta_{j,1}} [M_j - M_0 - (j-1)\theta_{j-1,2}\Gamma_{j-1} - \ldots - \theta_{j,j}\Gamma_1]$$

The relationship between the reconstructed value of $\bar{\mu}$ and the actual value of the attenuation coefficient $\mu$ depends upon the selection of function $\omega(\bar{r})$ which determines the parameters $M_j$ in the coefficients $\Gamma_j$. Assume for instance that it is a Gaussian function $$\omega(\bar{r}) = \frac{1}{\pi r_0^2} e^{-(\frac{\bar{r}}{r_0})^2} \qquad (6.12)$$

where the dimension $r_0$ is related to $r_1$ by $$r_0 = \lambda r_1 \qquad (6.13)$$

$\lambda$ being an arbitrary positive number. With the particular function $\omega$ given by Equation (6.12), in a first approximation, the value of $\bar{\mu}$ maintains the significance of an average value of the attenuation coefficient within a circle of radius $\lambda r_1$ and the coefficients $M_j$ become $$M_j = e^{-\frac{j}{\lambda^2}} - e^{-\frac{(j+1)^2}{\lambda^2}} \qquad (6.14)$$

TABLE IV

| j | =.250000 | =.500000 | =1.000000 | =2.000000 | =4.000000 | =10.000000 |
|---|---|---|---|---|---|---|
| 0 | .100000E+01 | .981684E+00 | .632121E+00 | .221199E+00 | .605869E−01 | .995017E−02 |
| 1 | −.577350E+00 | −.556201E+00 | −.163134E+00 | .109536E+00 | .577497E−01 | .111488E−01 |
| 2 | −.164130E+00 | −.166309E+00 | −.194570E+00 | −.352457E±01 | .380649E−01 | .110394E−01 |
| 3 | −.738420E−01 | −.742578E−01 | −.841560E−01 | −.775770E−01 | .129448E−01 | .100671E−01 |
| 4 | −.413549E−01 | −.414827E−01 | −.443852E−01 | −.575726E−01 | −.722496E−02 | .865788E−02 |
| 5 | −.263065E−01 | −.263575E−01 | −.274887E−01 | −.347911E−01 | −.183476E−01 | .699149E−02 |
| 6 | −.181722E−01 | −.181963E−01 | −.187244E−01 | −.219224E−01 | −.213030E−01 | .520595E−02 |
| 7 | −.132949E−01 | −.133077E−01 | −.135862E−01 | −.151109E−01 | −.193324E−01 | .342184E−02 |
| 8 | −.101451E−01 | −.101525E−01 | −.103130E−01 | −.111357E−01 | −.155668E−01 | .174130E−02 |
| 9 | −.799477E−02 | −.799934E−02 | −.809827E−02 | −.858510E−02 | −.118946E−01 | .243563E−03 |
| 10 | −.646205E−02 | −.646503E−02 | −.652929E−02 | −.683713E−02 | −.901663E−02 | −.101796E−02 |
| 11 | −.533133E−02 | −.533335E−02 | −.537689E−02 | −.558159E−02 | −.696186E−02 | −.201603E−02 |
| 12 | −.447342E−02 | −.447484E−02 | −.450539E−02 | −.464702E−02 | −.553060E−02 | −.274725E−02 |
| 13 | −.380715E−02 | −.380817E−02 | −.383023E−02 | −.393146E−02 | −.451774E−02 | −.322775E−02 |
| 14 | −.327940E−02 | −.328016E−02 | −.329649E−02 | −.337081E−02 | −.377651E−02 | −.348773E−02 |
| 15 | −.285428E−02 | −.285485E−02 | −.286720E−02 | −.292303E−02 | −.321459E−02 | −.356570E−02 |
| 16 | −.250679E−02 | −.250724E−02 | −.251674E−02 | −.255952E−02 | −.277564E−02 | −.350326E−02 |
| 17 | −.221913E−02 | −.221948E−02 | −.222692E−02 | −.226025E−02 | −.242448E−02 | −.334073E−02 |
| 18 | −.197831E−02 | −.197858E−02 | −.198449E−02 | −.201085E−02 | −.213822E−02 | −.311418E−02 |
| 19 | −.177467E−02 | −.177489E−02 | −.177964E−02 | −.180077E−02 | −.190126E−02 | −.285355E−02 |
| 20 | −.160094E−02 | −.160112E−02 | −.160498E−02 | −.162212E−02 | −.170256E−02 | −.258206E−02 |
| 21 | −.145154E−02 | −.145169E−02 | −.145486E−02 | −.146891E−02 | −.153413E−02 | −.231632E−02 |
| 22 | −.132212E−02 | −.132224E−02 | −.132487E−02 | −.133650E−02 | −.138998E−02 | −.206715E−02 |
| 23 | −.120928E−02 | −.120938E−02 | −.121158E−02 | −.122128E−02 | −.126558E−02 | −.184064E−02 |
| 24 | −.111029E−02 | −.111038E−02 | −.111223E−02 | −.112039E−02 | −.115741E−02 | −.163929E−02 |
| 25 | −.102298E−02 | −.102306E−02 | −.102463E−02 | −.103155E−02 | −.106273E−02 | −.146313E−02 |
| 26 | −.945586E−03 | −.945649E−03 | −.946990E−03 | −.952892E−03 | −.979364E−03 | −.131063E−02 |
| 27 | −.876654E−03 | −.876708E−03 | −.877861E−03 | −.882926E−03 | −.905546E−03 | −.117939E−02 |
| 28 | −.814996E−03 | −.815042E−03 | −.816038E−03 | −.820411E−03 | −.839959E−03 | −.106671E−02 |
| 29 | −.759623E−03 | −.759663E−03 | −.760528E−03 | −.764323E−03 | −.781139E−03 | −.969870E−03 |
| 30 | −.709709E−03 | −.709744E−03 | −.710499E−03 | −.713808E−03 | −.728426E−03 | −.886378E−03 |

Figure 18:
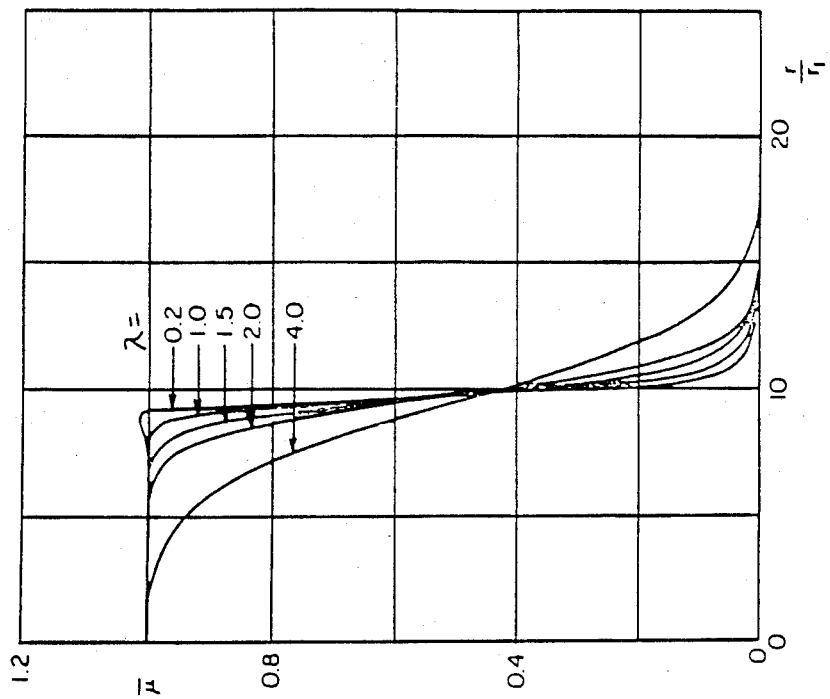
FIG. 18 shows the effect of a Gaussian weighting function on the spatial resolution of a reconstruction of a uniform cylinder.

The resulting values of $\Gamma j$ are shown in Table IV for several values of $\lambda$. In the limit of $\lambda$ small compared to unity, $$\lim_{\lambda \to 0} M = 1; \quad \lim_{\lambda \to 0} M_{j \neq 0} = 0 \qquad (6.15)$$

and $\Gamma_j$ reduces to the value of $F_j$, as is apparent from Table IV for $\lambda = 0.25$. Conversely in the limit of $\lambda$ large compared to unity, $\Gamma_j$ is positive for $j < \lambda$, consistent with the behavior of the coefficients $\overline{K}_j$, $\overline{K}_{o,j}$ which determine the average value of $\mu$ within the circle of radius $\lambda r_1$, in Equation (2.14). Of particular interest is the smooth transition from positive to negative values of $\Gamma_j$ for $\lambda \gg 1$, with a minimum value of $\Gamma_j$ found at j larger than $\lambda$ as shown in Table IV. Thus a value of $\lambda$ of the order, or smaller than unity, leads to a value of $\overline{\mu}$ close to the local value of $\mu$ as given by Equation (2.27), without altering the spatial resolution of the reconstructed image in any significant manner. An example of the effect of changing the parameter $\lambda$ Equation (6.14) is provided by the reconstruction of the $\overline{\mu}$ image of a uniform cylinder as shown in FIG. 18, (based on a computational simulation of attenuation data in a cylinder coaxial with the axis of scanning). The cylinder radius is equal to $10r_1$; FIG. 18 shows the values of $\overline{\mu}$ versus the radial distance from the axis for values of $\lambda$ equal to 0.25, 1, 1.5, 2, 4. The reconstruction of $\overline{\mu}$ across the boundary of the cylinder, at $r = 10r_1$, shows the increasing loss of spatial resolution above $\lambda = 1$. Outside of the cylinder the reconstruction error fluctuates about zero and Table V shows the effect of $\lambda$ on the values of $\overline{\mu}$ within the radial interval $70 < r/r_1 > 99$.

out a significant loss of spatial resolution. Equation (6.12) is only an example of a continuous function $\omega$, which yields an optimum form of the reconstruction algorithm as a trade-off between a value of $\overline{\mu}$ sufficiently close to $\mu$ and a minimum amplitude of the computational noise.

In this formulation of the reconstruction algorithm, the difference between local value $\mu$ and average value $<\mu>$, can be readily computed from Equation (6.9) as the difference between two values of $\overline{\mu}$ for $\lambda \sim 1$ and $\lambda \sim < 1$, i.e.

$$\mu - <\mu> \sim \frac{1}{4\pi r_1} \int_0^\pi |f_{\lambda \sim 1} - f_{\lambda \sim l}| d\psi \qquad (6.16)$$

Asymptotically for $j \gg 1$, one has $$\Gamma_j(\lambda \sim 1) - \Gamma_j(\lambda \sim l) \sim \frac{2}{\pi} \frac{1}{j^2} \qquad (6.17)$$

and the difference between the two values of $\Gamma_j$ for $\lambda \sim 1$, $\lambda \sim l$ decreases as $j^{-4}$. Thus solution (6.16) maintains the same properties of solution 2.23 of the problem of localized scanning. In the numerical applications of Equation (6.18), the reconstruction interpolation errors are generated primarily by the first term of the itegrand $(\lambda \sim 1)$. Consequently, the artifacts generated in the numerical reconstruction procedure of the $\mu - <\mu>$ image have essentially the same amplitude of the artifacts generated in the reconstruction of the local value of the attenuation coefficient.

Equation (6.14) represents the solution of the direct

TABLE V

| R/R1 | =0.25 | =1.00 | =1.50 | =2.00 | =4.00 |
|---|---|---|---|---|---|
| .99000E+02 | −.74756E−03 | −.217044E−03 | .249783E−04 | .315018E−04 | −.12950E−04 |
| .98000E+02 | −.37380E−02 | −.178138E−02 | −.677949E−03 | −.367232E−03 | −.81693E−04 |
| .97000E+02 | −.69320E−02 | −.358714E−02 | −.150025E−02 | −.763108E−03 | −.13642E−03 |
| .96000E+02 | −.10141E−01 | −.540831E−02 | −.233824E−02 | −.117515E−02 | −.21002E−03 |
| .95000E+02 | −.93699E−02 | −.492432E−02 | −.205338E−02 | −.100945E−02 | −.18377E−03 |
| .94000E+02 | −.66138E−02 | −.328842E−02 | −.120310E−02 | −.547142E−03 | −.12731E−03 |
| .93000E+02 | −.39392E−02 | −.174577E−02 | −.457485E−03 | −.157787E−03 | −.72186E−04 |
| .92000E+02 | −.13691E−02 | −.324347E−03 | .150706E−03 | .140403E−03 | .57641E−05 |
| .91000E+02 | .11879E−02 | .700432E−03 | .313436E−03 | .132251E−03 | .17880E−04 |
| .90000E+02 | .33729E−02 | .158540E−02 | .467702E−03 | .143026E−03 | .15827E−04 |
| .89000E+02 | .45014E−02 | .235809E−02 | .908587E−03 | .405469E−03 | .97493E−04 |
| .88000E+02 | .55441E−02 | .303988E−02 | .124678E−02 | .556555E−03 | .12360E−03 |
| .87000E+02 | .65729E−02 | .370779E−02 | .157099E−02 | .693512E−03 | .15605E−03 |
| .86000E+02 | .70248E−02 | .399090E−02 | .170359E−02 | .743631E−03 | .15229E−03 |
| .85000E+02 | .31792E−02 | .179735E−02 | .776416E−03 | .358307E−03 | .97608E−04 |
| .84000E+02 | −.69335E−03 | −.423523E−03 | −.178533E−03 | −.555437E−04 | .61978E−05 |
| .83000E+02 | −.46344E−02 | −.271753E−02 | −.121274E−02 | −.545647E−03 | −.12926E−03 |
| .82000E+02 | −.83592E−02 | −.498473E−02 | −.236067E−02 | −.112102E−02 | −.20656E−03 |
| .81000E+02 | −.54654E−02 | −.339375E−02 | −.159221E−02 | −.657532E−03 | −.10503E−03 |
| .80000E+02 | −.26544E−02 | −.189733E−02 | −.971910E−03 | −.370553E−03 | −.34637E−04 |
| .79000E+02 | .28291E−04 | −.489359E−03 | −.510177E−03 | −.292840E−03 | −.39820E−04 |
| .78000E+02 | .11563E−02 | .770354E−03 | .405253E−03 | .185032E−03 | .34493E−04 |
| .77000E+02 | .22317E−02 | .197570E−02 | .126268E−02 | .598178E−03 | .65952E−04 |
| .76000E+02 | .29734E−02 | .247217E−02 | .158058E−02 | .794099E−03 | .97960E−04 |
| .75000E+02 | .35697E−02 | .252617E−02 | .150811E−02 | .785963E−03 | .80164E−04 |
| .74000E+02 | .39666E−02 | .235006E−02 | .117572E−02 | .601905E−03 | .85774E−04 |
| .73000E+02 | −.10172E−03 | −.223963E−03 | −.216054E−03 | −.122017E−03 | .81227E−06 |
| .72000E+02 | −.50516E−02 | −.331927E−02 | −.190677E−02 | −.106602E−02 | −.12221E−03 |
| .71000E+02 | −.32284E−02 | −.249043E−02 | −.168228E−02 | −.101827E−02 | −.87943E−04 |
| .70000E+02 | −.84907E−03 | −.107589E−02 | −.996119E−03 | −.691295E−03 | −.57945E−04 |

The of $\lambda$ is particularly pronounced on the large error of $\overline{\mu}$ of the order of $-10^{-2}$ which is found in the proximity of $r/r_1 = 96$ for $\lambda = 0.25$. Table V shows that the error at $r/r_1 = 96$ decreases rapidly with increasing values of $\lambda$, and in particular the error is approximately halved for $\lambda = 1$. Hence a substantial improvement of the reconstruction interpolation error is achieved without a significant loss of spatial resolution. Equation problem of computing the values $\Gamma_j$ of the weighting function from a specified function of $\mu$ to be reconstructed in the image plane. The inverse problem can be stated: if a particular shape of the weighting function is specified, one may compute the function $\omega$ in Equation (6.11) and determine the relationship between the reconstructed value $\bar{\mu}$ and the actual attenuation coefficient.

From Equation (6.11) one obtains:

$$M_0 = \frac{1}{2}\Gamma_0 \qquad (6.18)$$

$$M_0 = \frac{1}{2}\Gamma_0 + \theta_{1,1}\Gamma_1$$

$$M_j = \frac{1}{2}\Gamma_0 + \theta_{1,j}\Gamma_1 + 2\theta_{2,j-1}\Gamma_2 + \ldots + j\theta_{j,1}\Gamma_g$$

Thus from Equation (6.6) the average value $\bar{\omega}_h$ of $\omega$ between the circles of radii $hr_1$ and $(h+1)r_1$ is $$\bar{\omega}_h \sim \frac{M_h}{(2h+1)\pi} r_1^2 \qquad (6.19)$$

and finally, by means of Equation (6.19), Equation (6.6) provides the value of $\bar{\mu}$ at each reconstruction point $O_r$.

EXAMPLES OF A $\Delta\mu$ IMAGE RECONSTRUCTION

Figure 19:
FIG. 19 is a reconstruction of the values of $\mu$ in a region of interest which was calculated from data obtained from a full scan of a body plane.
Figure 22:
FIGS. 20-23 are reconstructions of $\Delta\mu$ values in a region of interest which were calculated from data scanned in a limited part of the body plane.

FIGS. 19–23 illustrate the transition from a $\mu$ to a $\Delta\mu$ image obtained with different values of the parameter l. FIG. 19 is a reconstruction of $\mu$ values from data obtained in a Philips translational scanner (Tomoscan® 200 manufactured by Philips Medical Systems, Inc. Shelton, Conn. FIG. 19 is a partial reconstruction within a circular region which includes the liver, obtained with a full set of scanning data both inside and outside of the circle. The radius of the circle, normalized to $r_1l$, is equal to 127.

FIGS. 20–23 are a set of $\Delta\mu$ images for values l=60, 40, 20 and 5 obtained by ignoring scanning data outside of the circle of FIG. 19. The gray scale of each image consists of sixteen equally spaced gray levels; the middle level corresponds to $\Delta\mu=0$. Thus the images of FIGS. 20–23, present the full range of values of $\Delta\mu$ with the negative values corresponding to the darker half of the gray scale and the positive values corresponding to the lighter half. The images of FIGS. 14–23 are obtained by assuming that outside of the circle the value of $\beta$ an each radial line is constant and equal to the value measured on the circle for that particular line. The difference between the l=60 (FIG. 20) and l=40, (FIG. 21) images is minor and both are close to the conventional image of values shown in FIG. 17. The overall range of $\Delta\mu$ values of the reconstructed image decreases with decreasing values of l and the decrease in l results in a sharper transition across the interfaces as shown in the l=20 (FIG. 22) image. This becomes even more apparent in the l=5 (FIG. 23) image which reduces to the outline of the body organs with values of $\mu-<\mu>$ small everywhere else, (almost within the noise level); within the bone and in the soft tissue area as well.

Figure 21:
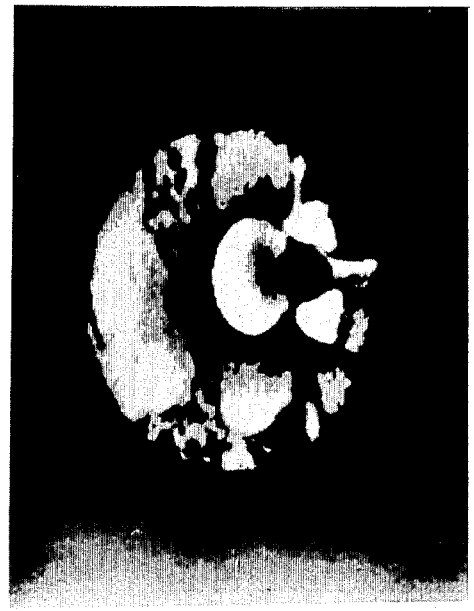
Figure 23:
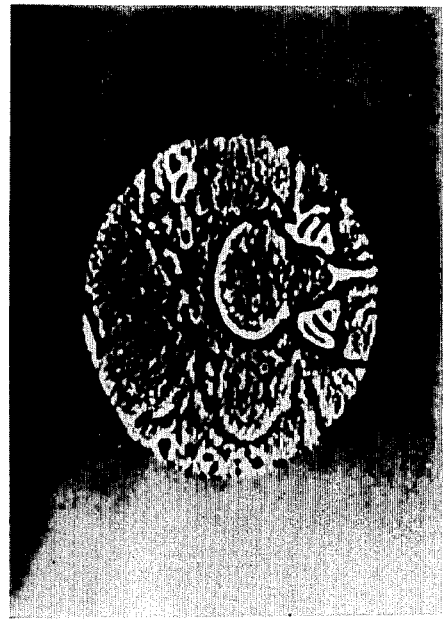
Figure 20:
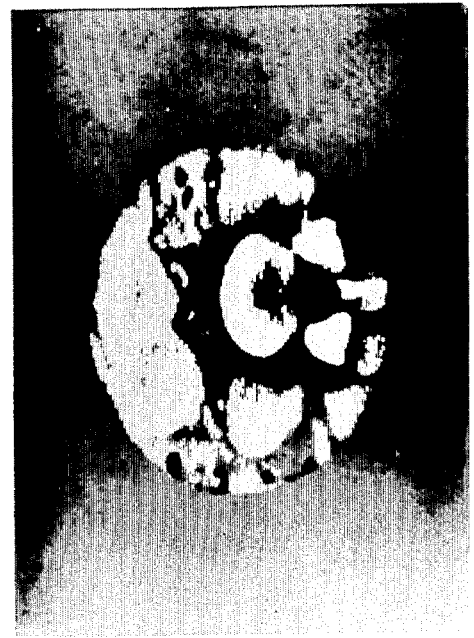

It is worthwhile pointing out that the lack of actual scanning data outside of the reconstruction circle has a negligible effect on the reconstruction of the images of FIGS. 20 and 21 and the image distortion is confined to a very small annular close to the boundary of the circle even for the larger values of l. This is the main reason why the $\Delta\mu$ algorithm allows a partial scanning of the area of interest.

The value of l represents an additional parameter in the display of a reconstructed image which can be used, for example, to enhance the geometry of interfaces in the area under scrutiny. In this connection it is worthwhile pointing out that for small values of l Equation (2.32) acquires the essential property of a local average of the second derivative of $\mu$. The value of $\mu-<\mu>$ is zero at the interface between two uniform media. Thus in a general situation of image reconstruction across sharp boundaries between media of different physical properties (like soft tissue-air interface of soft tissue-bone interface) the boundary would be described by one of the family of equations.

$$\mu-<\mu>=0$$

provided that the radius of the averaging circle is smaller than the local radius of curvature of the interface in the scanning plane. Hence $\Delta\mu$ images provide a very convenient tool to outline either bone or soft tissue interfaces without the need of computing the local values of the attenuation coefficient.

We claim:

1. A method for scanning a body as part of a process for reconstructing a cross-section thereof using a source of penetrating radiation that produces a plurality of coplanar beams defining a fan beam passing through the body coplanar with the cross-section, the method comprising:
   (a) positioning the fan beam relative to a spatially fixed center at a first position;
   (b) rotating the fan beam about the fixed center and measuring the intensity of each beam after it passes through the cross-section;
   (c) repositioning the fan beam relative to the fixed center to a second position; and
   (d) repeating step (b).

2. The method of claim 1 wherein the rotations are through substantially 360° and each rotation causes the fan beam to sweep out an area of the cross-section defined by reference circles concentric with the fixed center and tangent to the extremities of the fan beam.

3. The method of claim 2 wherein the positions of the fan beam are selected such that the swept out areas are contiguous.

* * * * *